(12) United States Patent
Apte et al.

(10) Patent No.: US 10,803,992 B2
(45) Date of Patent: *Oct. 13, 2020

(54) METHOD AND SYSTEM FOR MICROBIOME-DERIVED DIAGNOSTICS AND THERAPEUTICS FOR MENTAL HEALTH ASSOCIATED CONDITIONS

(71) Applicant: PSOMAGEN, INC., Rockville, MD (US)

(72) Inventors: Zachary Apte, San Francisco, CA (US); Daniel Almonacid, San Francisco, CA (US); Jessica Richman, San Francisco, CA (US)

(73) Assignee: PSOMAGEN, INC., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/668,595

(22) Filed: Aug. 3, 2017

(65) Prior Publication Data
US 2017/0327863 A1  Nov. 16, 2017

Related U.S. Application Data

(63) Continuation of application No. 15/098,236, filed on Apr. 13, 2016, which is a continuation-in-part of application No. 14/919,614, filed on Oct. 21, 2015, now Pat. No. 9,703,929.

(60) Provisional application No. 62/066,369, filed on Oct. 21, 2014, provisional application No. 62/087,551, filed on Dec. 4, 2014, provisional application No. 62/092,999, filed on Dec. 17, 2014, provisional application No. 62/147,376, filed on Apr. 14, 2015, provisional application No. 62/147,212, filed on Apr. 14, 2015, provisional application No. 62/147,362, filed on Apr. 14, 2015, provisional application No. 62/146,855, filed on Apr. 13, 2015, provisional application No. 62/206,654, filed on Aug. 18, 2015, provisional application No. 62/146,767, filed on Apr. 13, 2015, provisional application No. 62/146,818, filed on Apr. 13, 2015, provisional application No. 62/147,071, filed on Apr. 14, 2015, provisional application No. 62/147,287, filed on Apr. 14, 2015,
(Continued)

(51) Int. Cl.
| | |
|---|---|
| G01N 33/48 | (2006.01) |
| G16H 50/20 | (2018.01) |
| G06F 19/00 | (2018.01) |
| G16B 50/00 | (2019.01) |
| G16H 50/70 | (2018.01) |
| C12Q 1/04 | (2006.01) |
| C12Q 1/24 | (2006.01) |
| G01N 33/569 | (2006.01) |
| G16B 40/00 | (2019.01) |
| G16H 50/50 | (2018.01) |
| G16H 10/40 | (2018.01) |
| G16H 20/70 | (2018.01) |
| G06G 7/58 | (2006.01) |
| C12Q 1/00 | (2006.01) |

(52) U.S. Cl.
CPC .............. *G16H 50/20* (2018.01); *C12Q 1/04* (2013.01); *C12Q 1/24* (2013.01); *G01N 33/569* (2013.01); *G06F 19/324* (2013.01); *G06F 19/325* (2013.01); *G06F 19/3418* (2013.01); *G16B 40/00* (2019.02); *G16B 50/00* (2019.02); *G16H 10/40* (2018.01); *G16H 20/70* (2018.01); *G16H 50/50* (2018.01); *G16H 50/70* (2018.01); *C12Q 1/00* (2013.01); *G01N 2800/30* (2013.01); *G06F 19/00* (2013.01); *Y02A 90/26* (2018.01)

(58) Field of Classification Search
None
See application file for complete search history.

(56) References Cited

U.S. PATENT DOCUMENTS

| | | | |
|---|---|---|---|
| 6,033,864 | A | 3/2000 | Braun et al. |
| 6,309,643 | B1 | 10/2001 | Braun et al. |
| | | (Continued) | |

FOREIGN PATENT DOCUMENTS

| | | |
|---|---|---|
| CN | 105407728 | 3/2015 |
| EP | 2631240 | 8/2013 |
| | (Continued) | |

OTHER PUBLICATIONS

Benedict, et al., "Gut Microbiota and Glucometabolic Alterations in Response to Recurrent Partial Sleep Deprivation in Normal-Weight Young Individuals", Molecular Metabolism, vol. 5, 2016, pp. 1175-1186.

(Continued)

*Primary Examiner* — Eric S Dejong
(74) *Attorney, Agent, or Firm* — Lex IP Meister, PLLC

(57) ABSTRACT

A method for at least one of characterizing, diagnosing, and treating a mental health associated condition in at least a subject, the method comprising: receiving an aggregate set of biological samples from a population of subjects; generating at least one of a microbiome composition dataset and a microbiome functional diversity dataset for the population of subjects; generating a characterization of the mental health associated condition based upon features extracted from at least one of the microbiome composition dataset and the microbiome functional diversity dataset; based upon the characterization, generating a therapy model configured to correct the mental health associated condition; and at an output device associated with the subject, promoting a therapy to the subject based upon the characterization and the therapy model.

21 Claims, 6 Drawing Sheets

Related U.S. Application Data provisional application No. 62/147,314, filed on Apr. 14, 2015, provisional application No. 62/147,328, filed on Apr. 14, 2015, provisional application No. 62/147,337, filed on Apr. 14, 2015.

(56) References Cited

U.S. PATENT DOCUMENTS

| | | |
|---|---|---|
| 6,632,641 B1 | 10/2003 | Brennan et al. |
| 6,861,053 B1 | 3/2005 | Lin et al. |
| D521,843 S | 5/2006 | Hung |
| 7,048,906 B2 | 5/2006 | Lin et al. |
| 7,176,002 B2 | 2/2007 | Lao et al. |
| 8,478,544 B2 | 7/2013 | Colwell et al. |
| 8,598,203 B2 | 12/2013 | Tarcic et al. |
| 8,883,264 B2 | 11/2014 | Yang et al. |
| 9,028,841 B2 | 5/2015 | Henn et al. |
| 9,149,473 B2 | 10/2015 | Ecker et al. |
| 9,289,418 B2 | 3/2016 | Pimentel et al. |
| 9,433,651 B2 | 9/2016 | Jones et al. |
| 9,447,195 B2 | 9/2016 | Cordova et al. |
| 9,506,109 B2 | 11/2016 | Savelkoul et al. |
| 9,663,831 B2 | 5/2017 | Apte et al. |
| 9,700,586 B2 | 7/2017 | Bicalho et al. |
| 9,703,929 B2 | 7/2017 | Apte et al. |
| 9,707,207 B2 | 7/2017 | Finegold |
| 9,710,606 B2 | 7/2017 | Apte et al. |
| 2002/0012926 A1 | 1/2002 | Quake et al. |
| 2003/0190314 A1 | 10/2003 | Campbell et al. |
| 2005/0196785 A1 | 9/2005 | Quake et al. |
| 2006/0073501 A1 | 4/2006 | Van Den Boom et al. |
| 2006/0089310 A1 | 4/2006 | Goldstein et al. |
| 2007/0134652 A1 | 6/2007 | Slepnev et al. |
| 2007/0259337 A1 | 11/2007 | Hully et al. |
| 2008/0131556 A1 | 6/2008 | De Simone et al. |
| 2010/0035232 A1 | 2/2010 | Ecker et al. |
| 2010/0129816 A1 | 5/2010 | Savelkoul et al. |
| 2010/0172874 A1 | 7/2010 | Turnbaugh et al. |
| 2011/0027219 A1 | 2/2011 | Tarcic et al. |
| 2011/0177976 A1 | 7/2011 | Gordon et al. |
| 2012/0045771 A1 | 2/2012 | Beier et al. |
| 2012/0129794 A1 | 5/2012 | Dowd et al. |
| 2012/0149584 A1 | 6/2012 | Olle et al. |
| 2012/0252775 A1 | 10/2012 | Finegold |
| 2013/0017999 A1 | 1/2013 | Fremont et al. |
| 2013/0045874 A1 | 2/2013 | Ehrlich |
| 2013/0108598 A1 | 5/2013 | Oresic et al. |
| 2013/0121968 A1 | 5/2013 | Quay |
| 2013/0184302 A1 | 7/2013 | Bortey et al. |
| 2014/0093478 A1 | 4/2014 | Turnbaugh et al. |
| 2014/0136120 A1 | 5/2014 | Colwell et al. |
| 2014/0179726 A1 | 6/2014 | Bajaj et al. |
| 2014/0199281 A1 | 7/2014 | Henn et al. |
| 2014/0315929 A1 | 10/2014 | Chiosis |
| 2014/0341853 A1 | 11/2014 | Hovanky |
| 2014/0363399 A1 | 12/2014 | Jones et al. |
| 2015/0211055 A1 | 1/2015 | Apte et al. |
| 2015/0211078 A1 | 1/2015 | Apte et al. |
| 2015/0050245 A1 | 2/2015 | Herman et al. |
| 2015/0213193 A1 | 7/2015 | Apte et al. |
| 2015/0374761 A1 | 12/2015 | Sadowsky et al. |
| 2016/0032363 A1 | 2/2016 | Stintzi et al. |
| 2016/0040216 A1 | 2/2016 | Akins et al. |
| 2016/0110515 A1 | 4/2016 | Apte et al. |
| 2016/0228003 A1 | 4/2016 | Apte et al. |
| 2016/0138089 A1 | 5/2016 | Harris et al. |
| 2016/0223553 A1 | 8/2016 | Sears et al. |
| 2016/0290132 A1 | 10/2016 | Knight et al. |
| 2017/0024527 A1 | 1/2017 | Apte et al. |
| 2017/0039347 A1 | 2/2017 | Apte et al. |
| 2017/0081707 A1 | 3/2017 | Dillon et al. |
| 2017/0107557 A1 | 4/2017 | Embree et al. |
| 2017/0262608 A1 | 5/2017 | Apte et al. |
| 2017/0268045 A1 | 5/2017 | Apte et al. |
| 2017/0268046 A1 | 5/2017 | Apte et al. |
| 2017/0270268 A1 | 5/2017 | Apte et al. |
| 2017/0270269 A1 | 5/2017 | Apte et al. |
| 2017/0270270 A1 | 5/2017 | Apte et al. |
| 2017/0270271 A1 | 5/2017 | Apte et al. |
| 2017/0270272 A1 | 5/2017 | Apte et al. |
| 2017/0286619 A1 | 6/2017 | Apte et al. |
| 2017/0286620 A1 | 6/2017 | Apte et al. |
| 2017/0327864 A1 | 11/2017 | Apte et al. |
| 2017/0344719 A1 | 11/2017 | Apte et al. |
| 2017/0357763 A1 | 12/2017 | Apte et al. |
| 2017/0357767 A1 | 12/2017 | Apte et al. |
| 2017/0357768 A1 | 12/2017 | Apte et al. |
| 2017/0372027 A1 | 12/2017 | Apte et al. |
| 2018/0286520 A1 | 6/2018 | Apte et al. |
| 2019/0085396 A1 | 3/2019 | Apte et al. |

FOREIGN PATENT DOCUMENTS

| | | |
|---|---|---|
| EP | 2994756 | 3/2016 |
| WO | 039234 | 5/2003 |
| WO | 113066 | 9/2011 |
| WO | 050513 | 4/2012 |
| WO | 121298 | 8/2014 |
| WO | 138999 | 9/2014 |
| WO | 144092 | 9/2014 |
| WO | 145958 | 9/2014 |
| WO | 013214 | 1/2015 |
| WO | 2015/095241 A2 | 6/2015 |
| WO | 085326 | 6/2015 |
| WO | 103165 | 7/2015 |
| WO | 112352 | 7/2015 |
| WO | 170979 | 11/2015 |
| WO | 095241 | 12/2015 |
| WO | 2016/065075 A1 | 4/2016 |
| WO | 2015/112352 A8 | 6/2016 |
| WO | 138337 | 9/2016 |
| WO | 172643 | 10/2016 |
| WO | 2016/172643 A3 | 2/2017 |
| WO | 2017/044885 A1 | 3/2017 |
| WO | 044902 | 3/2017 |

OTHER PUBLICATIONS

Canadian Application No. 2,962,466, Examination Report dated Mar. 23, 2018, 4 pages.
European Application No. 15852829.9, Extended European Search Report dated May 14, 2018, 8 pages.
International Application No. PCT/US2018/035912, International Search Report and Written Opinion dated Sep. 12, 2018, 17 pages.
Kinross, et al., "Gut Microbiome-host Interactions in Health and Disease", Genome Medicine, vol. 3, No. 14, 2011, pp. 1-12.
Morgan, et al., "Biodiversity and Functional Genomics in the Human Microbiome", Trends Genet., vol. 29, No. 1, Jan. 2013, pp. 51-58.
Nagy-Szakal, et al., "Fecal Metagenomic Profiles in Subgroups of Patients with Myalgic Encephalomyelitis/Chronic Fatigue Syndrome", Microbiome, vol. 5, No. 44, 2017, pp. 1-17.
U.S. Appl. No. 15/606,743, Non-Final Office Action dated Dec. 19, 2017, 10 pages.
U.S. Appl. No. 15/606,743, Notice of Allowance dated Sep. 20, 2018, 5 pages.
U.S. Appl. No. 15/606,824, Final Office Action dated Sep. 20, 2018, 8 pages.
U.S. Appl. No. 15/606,824, Non-Final Office Action dated Jan. 16, 2018, 10 pages.
U.S. Appl. No. 15/606,874, Final Office Action dated Aug. 31, 2018, 8 pages.
U.S. Appl. No. 15/606,874, Non-Final Office Action dated Feb. 9, 2018, 10 pages.
U.S. Appl. No. 15/606,874, Notice of Allowance dated Jan. 17, 2019, 5 pages.
U.S. Appl. No. 15/606,909, Final Office Action dated Sep. 20, 2018, 8 pages.
U.S. Appl. No. 15/606,909, Non-Final Office Action dated Mar. 9, 2018, 10 pages.

(56) References Cited

OTHER PUBLICATIONS

U.S. Appl. No. 15/606,909, Notice of Allowance dated Feb. 20, 2019, 5 pages.
U.S. Appl. No. 15/606,943, Final Office Action dated Nov. 1, 2018, 7 pages.
U.S. Appl. No. 15/606,943, Non-Final Office Action dated Apr. 10, 2018, 10 pages.
U.S. Appl. No. 15/606,943, Notice of Allowance dated Mar. 8, 2019, 5 pages.
U.S. Appl. No. 15/606,975, Final Office Action dated Jun. 14, 2018, 8 pages.
U.S. Appl. No. 15/606,975, Non-Final Office Action dated Sep. 25, 2017, 10 pages.
U.S. Appl. No. 15/606,975, Notice of Allowance dated Oct. 19, 2018, 5 pages.
U.S. Appl. No. 15/621,144, Final Office Action dated Nov. 1, 2018, 7 pages.
U.S. Appl. No. 15/621,144, Non-Final Office Action dated Apr. 10, 2018, 10 pages.
U.S. Appl. No. 15/621,144, Notice of Allowance dated Mar. 8, 2019, 6 pages.
U.S. Appl. No. 15/621,152, Final Office Action dated Nov. 1, 2018, 7 pages.
U.S. Appl. No. 15/621,152, Non-Final Office Action dated Apr. 10, 2018, 10 pages.
U.S. Appl. No. 15/621,152, Notice of Allowance dated Mar. 8, 2019, 6 pages.
U.S. Appl. No. 15/997,654, Non-Final Office Action dated Nov. 1, 2018, 13 pages.
"K03100: lepB: signal pepidase I," KEGG, Aug. 7, 2012 (Aug. 7, 2012), p. 1 of 1. Retrieved from the Internet: on Jun. 12, 2016 (Jun. 12, 2016).
"KEGG: Aminoacyl-tRNA biosynthesis—Reference pathway," Jul. 20, 2013 (Jul. 20, 2013). Retrieved from the internet: <http://web:archive.org/web/20130720015616/http:www.genome.jp/kegg-bin/show_pathway?map=map00970&show_description=show. on Jun. 20, 2016, (Jun. 20, 2016).
Avila, Maria et al., The Oral Microbiota: Living with a Permanent Guest, DNA and Cell Biology, Nov. 8, 2009, vol. 28, No. 8.
Carroll et al. "Alterations in composition and diversity of the intestinal microbiota in patients with diarrhea-predominant irritable bowel syndrome," Feb. 20, 2012 (Feb. 29, 2012), vol. 24, pp. 1-19 [Original pp. 5215-5230] entire document.
Cho et al. "The Human Microbiome: at the Interface of Health and Disease," Nature Reviews Genetics, Apr. 1, 2012 (Apr. 1, 2012), vol. 13, pp. 260-270.
Dewhirst, Floyd et al., The Human Oral Microbiome, Journal of Bacteriology, Oct. 2010, vol. 192, No. 19, pp. 5002-5017.
Evans, Morgan, Prosthetic valve endocarditis due to *Neisseria elongata* subsp. *elongata* in a patient with Klinefelter's syndrome, Journal of Medical Microbiology, Jun. 1, 2007, vol. 56, No. 6, pp. 860-862.
Greenblum et al. "Metagenomic Systems Biology of the Human Gut Microbiome Reveals Topological Shifts Associated with Obesity and Inflammatory Bowel Disease," Proceeding of the National Academy of Sciences, Dec. 19, 2011 (Dec. 19, 2011), vol. 109, pp. 594-599.
Kanehisa et al. "KEGG: Kyoto encyclopedia of genes and genomes, "Nucleic Acids Research, Jan. 1, 2000 (Jan. 1, 2000), vol. 28, No. 1, pp. 27-30.
Mak et al. "MetaboLyzer: A Novel Statistical Workflow for Analyzing Post Processed LC/MS Metabolomics Data," Anal Chem, Jan. 7, 2014 (Jan. 7, 2014), vol. 86, pp. 506-513.
Morgan et al. "Dysfunction of the intestinal microbiome in inflammatory bowel disease and treatment," Genome Biol. Apr. 16, 2012 (Apr. 16, 2012), vol. 13(9):R79, pp. 1-18. entire document.
Mutlu et al. "A Compositional Look at the Human Gastrointestinal Microbiome and Immune Activation Parameters in HIV Infected Subjects," PLoS Pathogens, Feb. 20, 2014 (Feb. 20, 2014), vol. 10, pp. 1-18.
Nakayama et al. "Aberrant Structures of Fecal Bacterial Community in Allergic Infants Profiled by 16S rRNA Gene Pyrosequencing," FEMS Immunology & Medical Microbiology, Dec. 1, 2011 (Dec. 1, 2011), vol. 63, pp. 397-406.
Ponnusamy et al. "Microbial community and metabolomic comparison of irritable bowel syndrome faeces," Feb. 17, 2011 (Feb. 17, 2011), vol. 60, pp. 817-827. entire document.
International Application No. PCT/US2015/056767, International Preliminary Report on Patentability dated May 4, 2017, 9 pages.
International Application No. PCT/US2015/056767, International Search Report and Written Opinion dated Jan. 11, 2016, 10 pages.
International Application No. PCT/US2016/027365; International Preliminary Report on Patentability dated Oct. 17, 2017; 12 pages.
International Application No. PCT/US2016/027365, International Search Report and Written Opinion dated Jul. 27, 2016, 14 pages.
European Application No. 16780673.6; Supplementary European Search Report and Opinion dated Oct. 18, 2018; 11 pages.
U.S. Appl. No. 14/919,614, Non-Final Office Action dated Jul. 14, 2016, 10 pages.
U.S. Appl. No. 14/919,614, Notice of Allowance dated May 19, 2017, 10 pages.
U.S. Appl. No. 15/098,236, Non-Final Office Action dated Jul. 12, 2018, 14 pages.
U.S. Appl. No. 15/668,620, Non-Final Office Action dated Oct. 5, 2018, 13 pages.
U.S. Appl. No. 15/668,636, Non-Final Office Action dated Oct. 5, 2018, 12 pages.
U.S. Appl. No. 15/668,653, Non-Final Office Action dated Oct. 5, 2018, 13 pages.

METHOD AND SYSTEM FOR MICROBIOME-DERIVED DIAGNOSTICS AND THERAPEUTICS FOR MENTAL HEALTH ASSOCIATED CONDITIONS

CROSS-REFERENCE TO RELATED APPLICATIONS

This application is a continuation of U.S. application Ser. No. 15/098,236, filed 13 Apr. 2016, which is a continuation-in-part of U.S. application Ser. No. 14/919,614 filed 21 Oct. 2015, which claims the benefit of U.S. Provisional Application Ser. No. 62/066,369 filed 21 Oct. 2014, U.S. Provisional Application Ser. No. 62/087,551 filed 4 Dec. 2014, U.S. Provisional Application Ser. No. 62/092,999 filed 17 Dec. 2014, U.S. Provisional Application Ser. No. 62/147,376 filed 14 Apr. 2015, U.S. Provisional Application Ser. No. 62/147,212 filed 14 Apr. 2015, U.S. Provisional Application Ser. No. 62/147,362 filed 14 Apr. 2015, U.S. Provisional Application Ser. No. 62/146,855 filed 13 Apr. 2015, and U.S. Provisional Application Ser. No. 62/206,654 filed 18 Aug. 2015, which are each incorporated in its entirety herein by this reference.

This application is a continuation of U.S. application Ser. No. 15/098,236, filed 13 Apr. 2016, which claims the benefit of U.S. Provisional Application Ser. No. 62/146,767 filed 13 Apr. 2015, U.S. Provisional Application Ser. No. 62/146,818 filed 13 Apr. 2015, U.S. Provisional Application Ser. No. 62/147,071 filed 14 Apr. 2015, U.S. Provisional Application Ser. No. 62/147,287 filed 14 Apr. 2015, U.S. Provisional Application Ser. No. 62/147,314 filed 14 Apr. 2015, U.S. Provisional Application Ser. No. 62/147,328 filed 14 Apr. 2015, and U.S. Provisional Application Ser. No. 62/147,337 filed 14 Apr. 2015, which are each incorporated in its entirety herein by this reference

TECHNICAL FIELD

This invention relates generally to the field of mental health and more specifically to a new and useful method and system for microbiome-derived diagnostics and therapeutics in the field of mental health.

BACKGROUND

A microbiome is an ecological community of commensal, symbiotic, and pathogenic microorganisms that are associated with an organism. The human microbiome comprises as many microbial cells as human cells present in the entire human body, but characterization of the human microbiome is still in nascent stages due to limitations in sample processing techniques, genetic analysis techniques, and resources for processing large amounts of data. Nonetheless, the microbiome is suspected to play at least a partial role in a number of health/disease-related states (e.g., preparation for childbirth, gastrointestinal disorders, etc.).

Given the profound implications of the microbiome in affecting a subject's health, efforts related to the characterization of the microbiome, the generation of insights from the characterization, and the generation of therapeutics configured to rectify states of dysbiosis should be pursued. Current methods and systems for analyzing the microbiomes of humans and providing therapeutic measures based on gained insights have, however, left many questions unanswered. In particular, methods for characterizing certain health conditions and therapies (e.g., probiotic therapies) tailored to specific subjects have not been viable due to limitations in current technologies.

As such, there is a need in the field of microbiology for a new and useful method and system for characterizing mental health associated conditions in an individualized and population-wide manner. This invention creates such a new and useful method and system.

DESCRIPTION OF THE EMBODIMENTS

The following description of the embodiments of the invention is not intended to limit the invention to these embodiments, but rather to enable any person skilled in the art to make and use this invention.

Figure 1A:
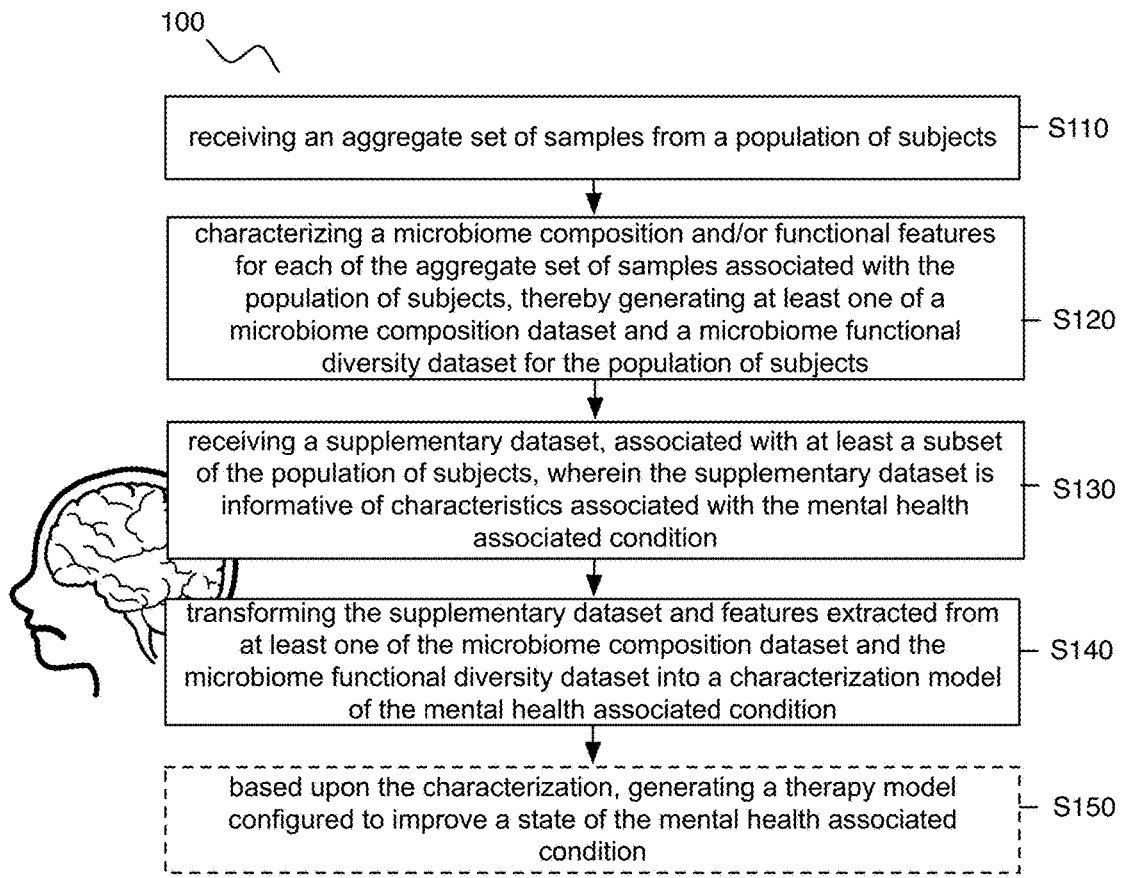
FIG. 1A is a flowchart of an embodiment of a method characterizing a microbiome-derived condition and identifying therapeutic measures.

1. Method for Characterizing a Microbiome-Derived Condition and Identifying Therapeutic Measures As shown in FIG. 1A, a first method 100 for diagnosing and treating a mental health associated condition comprises: receiving an aggregate set of samples from a population of subjects S110; characterizing a microbiome composition and/or functional features for each of the aggregate set of samples associated with the population of subjects, thereby generating at least one of a microbiome composition dataset and a microbiome functional diversity dataset for the population of subjects S120; receiving a supplementary dataset, associated with at least a subset of the population of subjects, wherein the supplementary dataset is informative of characteristics associated with the mental health associated condition S130; and transforming the supplementary dataset and features extracted from at least one of the microbiome composition dataset and the microbiome functional diversity dataset into a characterization model of the mental health associated condition S140. In some variations, the first method 100 can further include: based upon the characterization, generating a therapy model configured to improve a state of the mental health associated conditions S150.

The first method 100 functions to generate models that can be used to characterize and/or diagnose subjects according to at least one of their microbiome composition and functional features (e.g., as a clinical diagnostic, as a companion diagnostic, etc.), and provide therapeutic measures (e.g., probiotic-based therapeutic measures, phage-based therapeutic measures, small-molecule-based therapeutic measures, prebiotic-based therapeutic measures, clinical measures, etc.) to subjects based upon microbiome analysis for a population of subjects. As such, data from the population of subjects can be used to characterize subjects according to their microbiome composition and/or functional features, indicate states of health and areas of improvement based upon the characterization(s), and promote one or more therapies that can modulate the composition of a subject's microbiome toward one or more of a set of desired equilibrium states.

In variations, the method 100 can be used to promote targeted therapies to subjects suffering from a mental health associated condition, disorder, or adverse state, wherein the mental health associated condition produces psychological and/or physiological effects in relation to one or more of: energy levels, mood, depression, anxiety, motor ability, and any other suitable physiological or behavioral function. In more detail, conditions targeted by the method 100 can be described by one or more comorbidities, and in specific examples, can be characterized by one or more of the following comorbidities: mental health, cardiovascular disease, and chronic lung disease. In these variations, diagnostics associated with the mental health associated condition and/or other comorbidities can be typically assessed using one or more of: a blood test, endoscopy, biopsy, imaging based method, a behavioral survey instrument (e.g., a Patient Health Questionnaire-9 (PHQ-9) survey, a patient health questionnaire-2 (PHQ-2) survey, an instrument derived from an edition of the Diagnostic and Statistical Manual (DSM) of mental disorders, and any other standard method. In specific examples, the method 100 can be used for characterization of and/or therapeutic intervention for one or more of: Acid reflux/gastroesophageal reflux disease (GERD), multiple sclerosis (MS), acquired immune deficiency syndrome (AIDS), colorectal cancer, Parkinson's disease, Sjogren's syndrome, and stroke, wherein mental health is a comorbidity of acid reflux/GERD and stroke; cardiovascular disease is a comorbidity of AIDS, colorectal cancer, Parkinsons disease, and stroke; and MS and Sjogren's syndrome are comorbidities of chronic lung disease. As such, the method 100 can be used to characterize mental health associated conditions, disorders, and/or adverse states in an entirely non-typical method.

In particular, the inventors propose that characterization of the microbiome of individuals can be useful for predicting the likelihood of occurrence of mental health associated conditions in subjects. Such characterizations can also be useful for screening for mental health associated conditions and/or determining a course of treatment for an individual human with a mental health associated condition. For example, by deep sequencing bacterial DNAs from diseased and healthy subjects, the inventors propose that features associated with certain microbiome compositional and/or functional features (e.g., the amount of certain bacteria and/or bacterial sequences corresponding to certain genetic pathways) can be used to predict the presence or absence of a mental health associated condition. The bacteria and genetic pathways in some cases are present in a certain abundance in individuals having various mental health associated conditions as discussed in more detail below whereas the bacteria and genetic pathways are at a statistically different abundance in individuals not having the mental health associated condition.

Figure 1B:
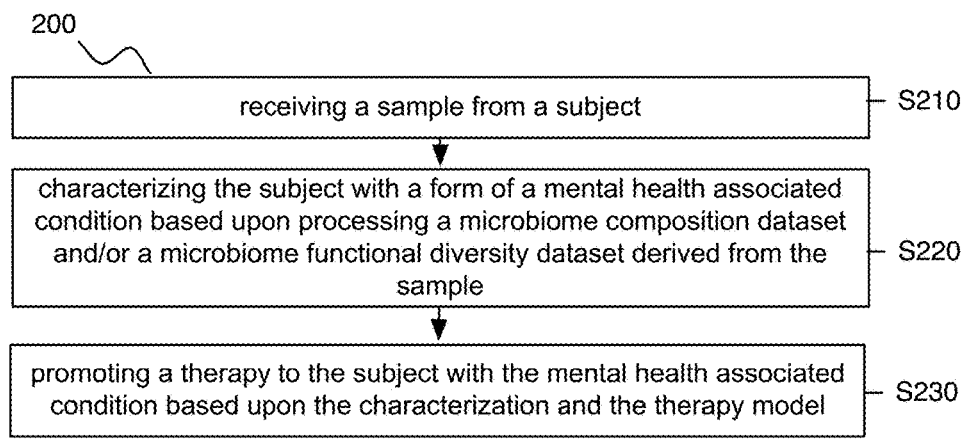
FIG. 1B is a flowchart of an embodiment of a method for generating microbiome-derived diagnostics.

As such, in some embodiments, outputs of the first method 100 can be used to generate diagnostics and/or provide therapeutic measures for a subject based upon an analysis of the subject's microbiome composition and/or functional features of the subject's microbiome. Thus, as shown in FIG. 1B, a second method 200 derived from at least one output of the first method 100 can include: receiving a biological sample from a subject S210; characterizing the subject with a form of an a mental health associated condition based upon processing a microbiome dataset derived from the biological sample S220; and promoting a therapy to the subject with the mental health associated condition based upon the characterization and the therapy model S230. Variations of the method 100 can further facilitate monitoring and/or adjusting of therapies provided to a subject, for instance, through reception, processing, and analysis of additional samples from a subject throughout the course of therapy. Embodiments, variations, and examples of the second method 200 are described in more detail below.

The methods thus 100, 200 function to generate models that can be used to classify individuals and/or provide therapeutic measures (e.g., therapy recommendations, therapies, therapy regimens, etc.) to individuals based upon microbiome analysis for a population of individuals. As such, data from the population of individuals can be used to generate models that can classify individuals according to their microbiome compositions (e.g., as a diagnostic measure), indicate states of health and areas of improvement based upon the classification(s), and/or provide therapeutic measures that can push the composition of an individual's microbiome toward one or more of a set of improved equilibrium states. Variations of the second method 200 can further facilitate monitoring and/or adjusting of therapies provided to an individual, for instance, through reception, processing, and analysis of additional samples from an individual throughout the course of therapy.

Figure 2:
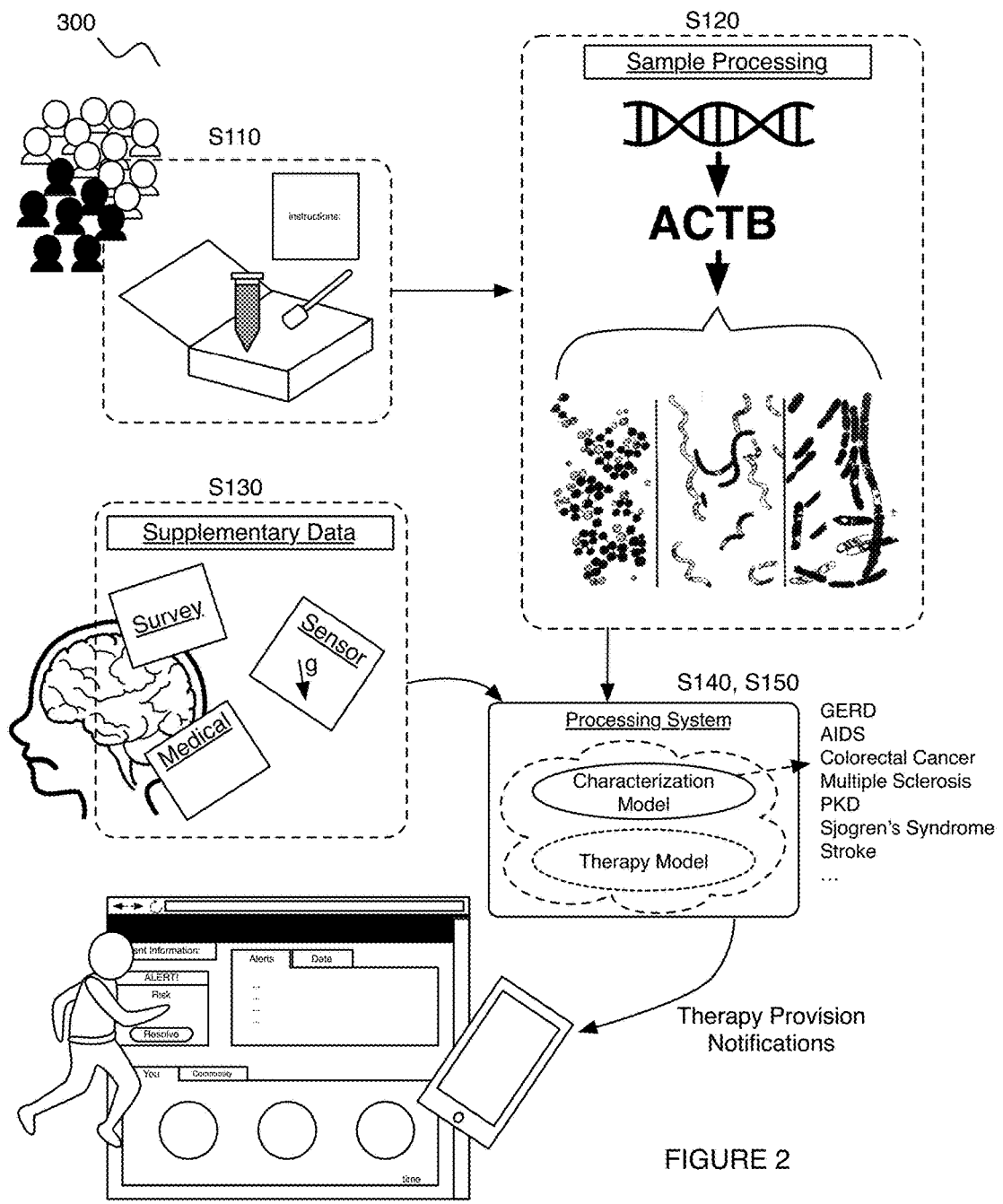
FIG. 2 depicts an embodiment of a method and system for generating microbiome-derived diagnostics and therapeutics.

In one application, at least one of the methods 100, 200 is implemented, at least in part, at a system 300, as shown in FIG. 2, that receives a biological sample derived from the subject (or an environment associated with the subject) by way of a sample reception kit, and processes the biological sample at a processing system implementing a characterization process and a therapy model configured to positively influence a microorganism distribution in the subject (e.g., human, non-human animal, environmental ecosystem, etc.). In variations of the application, the processing system can be configured to generate and/or improve the characterization process and the therapy model based upon sample data received from a population of subjects. The method 100 can, however, alternatively be implemented using any other suitable system(s) configured to receive and process microbiome-related data of subjects, in aggregation with other information, in order to generate models for microbiome-derived diagnostics and associated therapeutics. Thus, the method 100 can be implemented for a population of subjects (e.g., including the subject, excluding the subject), wherein the population of subjects can include patients dissimilar to and/or similar to the subject (e.g., in health condition, in dietary needs, in demographic features, etc.). Thus, information derived from the population of subjects can be used to provide additional insight into connections between behaviors of a subject and effects on the subject's microbiome, due to aggregation of data from a population of subjects.

Thus, the methods 100, 200 can be implemented for a population of subjects (e.g., including the subject, excluding the subject), wherein the population of subjects can include subjects dissimilar to and/or similar to the subject (e.g., health condition, in dietary needs, in demographic features, etc.). Thus, information derived from the population of subjects can be used to provide additional insight into connections between behaviors of a subject and effects on the subject's microbiome, due to aggregation of data from a population of subjects.

1.1 First Method: Sample Handling

Block S110 recites: receiving an aggregate set of biological samples from a population of subjects, which functions to enable generation of data from which models for characterizing subjects and/or providing therapeutic measures to subjects can be generated. In Block S110, biological samples are preferably received from subjects of the population of subjects in a non-invasive manner. In variations, non-invasive manners of sample reception can use any one or more of: a permeable substrate (e.g., a swab configured to wipe a region of a subject's body, toilet paper, a sponge, etc.), a non-permeable substrate (e.g., a slide, tape, etc.), a container (e.g., vial, tube, bag, etc.) configured to receive a sample from a region of a subject's body, and any other suitable sample-reception element. In a specific example, samples can be collected from one or more of a subject's nose, skin, genitals, mouth, and gut in a non-invasive manner (e.g., using a swab and a vial). However, one or more biological samples of the set of biological samples can additionally or alternatively be received in a semi-invasive manner or an invasive manner. In variations, invasive manners of sample reception can use any one or more of: a needle, a syringe, a biopsy element, a lance, and any other suitable instrument for collection of a sample in a semi-invasive or invasive manner. In specific examples, samples can comprise blood samples, plasma/serum samples (e.g., to enable extraction of cell-free DNA), and tissue samples.

In the above variations and examples, samples can be taken from the bodies of subjects without facilitation by another entity (e.g., a caretaker associated with an individual, a health care professional, an automated or semi-automated sample collection apparatus, etc.), or can alternatively be taken from bodies of individuals with the assistance of another entity. In one example, wherein samples are taken from the bodies of subjects without facilitation by another entity in the sample extraction process, a sample-provision kit can be provided to a subject. In the example, the kit can include one or more swabs for sample acquisition, one or more containers configured to receive the swab(s) for storage, instructions for sample provision and setup of a user account, elements configured to associate the sample(s) with the subject (e.g., barcode identifiers, tags, etc.), and a receptacle that allows the sample(s) from the individual to be delivered to a sample processing operation (e.g., by a mail delivery system). In another example, wherein samples are extracted from the user with the help of another entity, one or more samples can be collected in a clinical or research setting from a subject (e.g., during a clinical appointment).

In Block S110, the aggregate set of biological samples is preferably received from a wide variety of subjects, and can involve samples from human subjects and/or non-human subjects. In relation to human subjects, Block S110 can include receiving samples from a wide variety of human subjects, collectively including subjects of one or more of: different demographics (e.g., genders, ages, marital statuses, ethnicities, nationalities, socioeconomic statuses, sexual orientations, etc.), different health conditions (e.g., health and disease states), different living situations (e.g., living alone, living with pets, living with a significant other, living with children, etc.), different dietary habits (e.g., omnivorous, vegetarian, vegan, sugar consumption, acid consumption, etc.), different behavioral tendencies (e.g., levels of physical activity, drug use, alcohol use, etc.), different levels of mobility (e.g., related to distance traveled within a given time period), biomarker states (e.g., cholesterol levels, lipid levels, etc.), weight, height, body mass index, genotypic factors, and any other suitable trait that has an effect on microbiome composition. As such, as the number of subjects increases, the predictive power of feature-based models generated in subsequent blocks of the method too increases, in relation to characterizing a variety of subjects based upon their microbiomes. Additionally or alternatively, the aggregate set of biological samples received in Block S110 can include receiving biological samples from a targeted group of similar subjects in one or more of: demographic traits, health conditions, living situations, dietary habits, behavior tendencies, levels of mobility, age range (e.g., pediatric, adulthood, geriatric), and any other suitable trait that has an effect on microbiome composition. Additionally or alternatively, the methods 100, 200 can be adapted to characterize conditions typically detected by way of lab tests (e.g., polymerase chain reaction based tests, cell culture based tests, blood tests, biopsies, chemical tests, etc.), physical detection methods (e.g., manometry), medical history based assessments, behavioral assessments, and imagenology based assessments. Additionally or alternatively, the methods 100, 200 can be adapted to characterization of acute conditions, chronic conditions, conditions with difference in prevalence for different demographics, conditions having characteristic disease areas (e.g., the head, the gut, endocrine system diseases, the heart, nervous system diseases, respiratory diseases, immune system diseases, circulatory system diseases, renal system diseases, locomotor system diseases, etc.), and comorbid conditions.

In some embodiments, receiving the aggregate set of biological samples in Block S110 can be performed according to embodiments, variations, and examples of sample reception as described in U.S. application Ser. No. 14/593,424 filed on 9 Jan. 2015 and entitled "Method and System for Microbiome Analysis", which is incorporated herein in its entirety by this reference. However, receiving the aggregate set of biological samples in Block S110 can additionally or alternatively be performed in any other suitable manner. Furthermore, some variations of the first method 100 can omit Block S100, with processing of data derived from a set of biological samples performed as described below in subsequent blocks of the method 100.

1.2 First Method: Sample Analysis, Microbiome Composition, and Functional Aspects Block S120 recites: characterizing a microbiome composition and/or functional features for each of the aggregate set of biological samples associated with a population of subjects, thereby generating at least one of a microbiome composition dataset and a microbiome functional diversity dataset for the population of subjects. Block S120 functions to process each of the aggregate set of biological samples, in order to determine compositional and/or functional aspects associated with the microbiome of each of a population of subjects. Compositional and functional aspects can include compositional aspects at the microorganism level, including parameters related to distribution of microorganisms across different groups of kingdoms, phyla, classes, orders, families, genera, species, subspecies, strains, infraspecies taxon (e.g., as measured in total abundance of each group, relative abundance of each group, total number of groups represented, etc.), and/or any other suitable taxa. Compositional and functional aspects can also be represented in terms of operational taxonomic units (OTUs). Compositional and functional aspects can additionally or alternatively include compositional aspects at the genetic level (e.g., regions determined by multilocus sequence typing, 16S sequences, 18S sequences, ITS sequences, other genetic markers, other phylogenetic markers, etc.). Compositional and functional aspects can include the presence or absence or the quantity of genes associated with specific functions (e.g., enzyme activities, transport functions, immune activities, etc.). Outputs of Block S120 can thus be used to provide features of interest for the characterization process of Block S140, wherein the features can be microorganism-based (e.g., presence of a genus of bacteria), genetic-based (e.g., based upon representation of specific genetic regions and/or sequences) and/or functional-based (e.g., presence of a specific catalytic activity, presence of metabolic pathways, etc.).

In one variation, Block S120 can include characterization of features based upon identification of phylogenetic markers derived from bacteria and/or archaea in relation to gene families associated with one or more of: ribosomal protein S2, ribosomal protein S3, ribosomal protein S5, ribosomal protein S7, ribosomal protein S8, ribosomal protein S9, ribosomal protein S10, ribosomal protein S11, ribosomal protein S12/S23, ribosomal protein S13, ribosomal protein S15P/S13e, ribosomal protein S17, ribosomal protein S19, ribosomal protein L1, ribosomal protein L2, ribosomal protein L3, ribosomal protein L4/L1e, ribosomal protein L5, ribosomal protein L6, ribosomal protein L10, ribosomal protein L11, ribosomal protein L13, ribosomal protein L14b/L23e, ribosomal protein L15, ribosomal protein L16/L10E, ribosomal protein L18P/L5E, ribosomal protein L22, ribosomal protein L24, ribosomal protein L25/L23, ribosomal protein L29, translation elongation factor EF-2, translation initiation factor IF-2, metalloendopeptidase, ffh signal recognition particle protein, phenylalanyl-tRNA synthetase alpha subunit, phenylalanyl-tRNA synthetase beta subunit, tRNA pseudouridine synthase B, porphobilinogen deaminase, phosphoribosylformylglycinamidine cyclo-ligase, and ribonuclease HII. However, the markers can include any other suitable marker(s)

Characterizing the microbiome composition and/or functional features for each of the aggregate set of biological samples in Block S120 thus preferably includes a combination of sample processing techniques (e.g., wet laboratory techniques) and computational techniques (e.g., utilizing tools of bioinformatics) to quantitatively and/or qualitatively characterize the microbiome and functional features associated with each biological sample from a subject or population of subjects.

In variations, sample processing in Block S120 can include any one or more of: lysing a biological sample, disrupting membranes in cells of a biological sample, separation of undesired elements (e.g., RNA, proteins) from the biological sample, purification of nucleic acids (e.g., DNA) in a biological sample, amplification of nucleic acids from the biological sample, further purification of amplified nucleic acids of the biological sample, and sequencing of amplified nucleic acids of the biological sample. Thus, portions of Block S120 can be implemented using embodiments, variations, and examples of the sample handling network and/or computing system as described in U.S. application Ser. No. 14/593,424 filed on 9 Jan. 2015 and entitled "Method and System for Microbiome Analysis", which is incorporated herein in its entirety by this reference. Thus the computing system implementing one or more portions of the method 100 can be implemented in one or more computing systems, wherein the computing system(s) can be implemented at least in part in the cloud and/or as a machine (e.g., computing machine, server, mobile computing device, etc.) configured to receive a computer-readable medium storing computer-readable instructions. However, Block S120 can be performed using any other suitable system(s).

In variations, lysing a biological sample and/or disrupting membranes in cells of a biological sample preferably includes physical methods (e.g., bead beating, nitrogen decompression, homogenization, sonication), which omit certain reagents that produce bias in representation of certain bacterial groups upon sequencing. Additionally or alternatively, lysing or disrupting in Block S120 can involve chemical methods (e.g., using a detergent, using a solvent, using a surfactant, etc.). Additionally or alternatively, lysing or disrupting in Block S120 can involve biological methods.

In variations, separation of undesired elements can include removal of RNA using RNases and/or removal of proteins using proteases. In variations, purification of nucleic acids can include one or more of: precipitation of nucleic acids from the biological samples (e.g., using alcohol-based precipitation methods), liquid-liquid based purification techniques (e.g., phenol-chloroform extraction), chromatography-based purification techniques (e.g., column adsorption), purification techniques involving use of binding moiety-bound particles (e.g., magnetic beads, buoyant beads, beads with size distributions, ultrasonically responsive beads, etc.) configured to bind nucleic acids and configured to release nucleic acids in the presence of an elution environment (e.g., having an elution solution, providing a pH shift, providing a temperature shift, etc.), and any other suitable purification techniques.

In variations, performing an amplification operation S123 on purified nucleic acids can include performing one or more of: polymerase chain reaction (PCR)-based techniques (e.g., solid-phase PCR, RT-PCR, qPCR, multiplex PCR, touchdown PCR, nanoPCR, nested PCR, hot start PCR, etc.), helicase-dependent amplification (HDA), loop mediated isothermal amplification (LAMP), self-sustained sequence replication (3SR), nucleic acid sequence based amplification (NASBA), strand displacement amplification (SDA), rolling circle amplification (RCA), ligase chain reaction (LCR), and any other suitable amplification technique. In amplification of purified nucleic acids, the primers used are preferably selected to prevent or minimize amplification bias, as well as configured to amplify nucleic acid regions/sequences (e.g., of the 16S region, the 18S region, the ITS region, etc.) that are informative taxonomically, phylogenetically, for diagnostics, for formulations (e.g., for probiotic formulations), and/or for any other suitable purpose. Thus, universal primers (e.g., a F27-R338 primer set for 16S RNA, a F515-R806 primer set for 16S RNA, etc.) configured to avoid amplification bias can be used in amplification. Primers used in variations of Block S110 can additionally or alternatively include incorporated barcode sequences specific to each biological sample, which can facilitate identification of biological samples post-amplification. Primers used in variations of Block S110 can additionally or alternatively include adaptor regions configured to cooperate with sequencing techniques involving complementary adaptors (e.g., according to protocols for Illumina Sequencing).

Identification of a primer set for a multiplexed amplification operation can be performed according to embodiments, variations, and examples of methods described in U.S. App. No. 62/206,654 filed 18 Aug. 2015 and entitled "Method and System for Multiplex Primer Design", which is herein incorporated in its entirety by this reference. Performing a multiplexed amplification operation using a set of primers in Block S123 can additionally or alternatively be performed in any other suitable manner.

Figure 3:
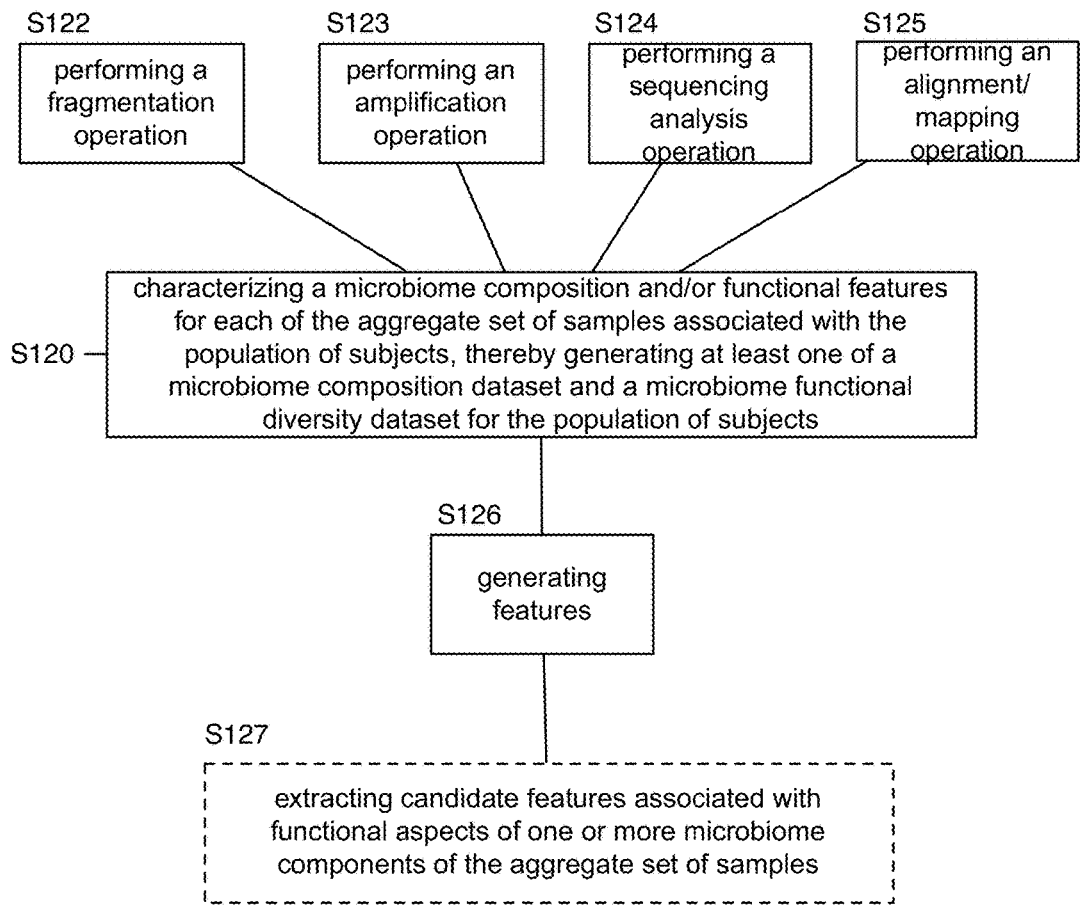
FIG. 3 depicts variations of a portion of an embodiment of a method for generating microbiome-derived diagnostics and therapeutics.

Additionally or alternatively, as shown in FIG. 3, Block S120 can implement any other step configured to facilitate processing (e.g., using a Nextera kit) for performance of a fragmentation operation S122 (e.g., fragmentation and tagging with sequencing adaptors) in cooperation with the amplification operation S123 (e.g., S122 can be performed after S123, S122 can be performed before S123, S122 can be performed substantially contemporaneously with S123, etc.) Furthermore, Blocks S122 and/or S123 can be performed with or without a nucleic acid extraction step. For instance, extraction can be performed prior to amplification of nucleic acids, followed by fragmentation, and then amplification of fragments. Alternatively, extraction can be performed, followed by fragmentation and then amplification of fragments. As such, in some embodiments, performing an amplification operation in Block S123 can be performed according to embodiments, variations, and examples of amplification as described in U.S. application Ser. No. 14/593,424 filed on 9 Jan. 2015 and entitled "Method and System for Microbiome Analysis". Furthermore, amplification in Block S123 can additionally or alternatively be performed in any other suitable manner.

In a specific example, amplification and sequencing of nucleic acids from biological samples of the set of biological samples includes: solid-phase PCR involving bridge amplification of DNA fragments of the biological samples on a substrate with oligo adapters, wherein amplification involves primers having a forward index sequence (e.g., corresponding to an Illumina forward index for MiSeq/NextSeq/HiSeq platforms) or a reverse index sequence (e.g., corresponding to an Illumina reverse index for MiSeq/NextSeq/HiSeq platforms), a forward barcode sequence or a reverse barcode sequence, a transposase sequence (e.g., corresponding to a transposase binding site for MiSeq/NextSeq/HiSeq platforms), a linker (e.g., a zero, one, or two-base fragment configured to reduce homogeneity and improve sequence results), an additional random base, and a sequence for targeting a specific target region (e.g., 16S region, 18S region, ITS region). Amplification and sequencing can further be performed on any suitable amplicon, as indicated throughout the disclosure. In the specific example, sequencing comprises Illumina sequencing (e.g., with a HiSeq platform, with a MiSeq platform, with a NextSeq platform, etc.) using a sequencing-by-synthesis technique. Additionally or alternatively, any other suitable next generation sequencing technology (e.g., PacBio platform, MinION platform, Oxford Nanopore platform, etc.) can be used. Additionally or alternatively, any other suitable sequencing platform or method can be used (e.g., a Roche 454 Life Sciences platform, a Life Technologies SOLiD platform, etc.). In examples, sequencing can include deep sequencing to quantify the number of copies of a particular sequence in a sample and then also be used to determine the relative abundance of different sequences in a sample. Deep sequencing refers to highly redundant sequencing of a nucleic acid sequence, for example such that the original number of copies of a sequence in a sample can be determined or estimated. The redundancy (i.e., depth) of the sequencing is determined by the length of the sequence to be determined (X), the number of sequencing reads (N), and the average read length (L). The redundancy is then N×L/X. The sequencing depth can be, or be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 70, 80, 90, 100, 110, 120, 130, 150, 200, 300, 500, 500, 700, 1000, 2000, 3000, 4000, 5000 or more.

Some variations of sample processing in Block S120 can include further purification of amplified nucleic acids (e.g., PCR products) prior to sequencing, which functions to remove excess amplification elements (e.g., primers, dNTPs, enzymes, salts, etc.). In examples, additional purification can be facilitated using any one or more of: purification kits, buffers, alcohols, pH indicators, chaotropic salts, nucleic acid binding filters, centrifugation, and any other suitable purification technique.

In variations, computational processing in Block S120 can include any one or more of: performing a sequencing analysis operation S124 including identification of microbiome-derived sequences (e.g., as opposed to subject sequences and contaminants), performing an alignment and/or mapping operation S125 of microbiome-derived sequences (e.g., alignment of fragmented sequences using one or more of single-ended alignment, ungapped alignment, gapped alignment, pairing), and generating features S126 derived from compositional and/or functional aspects of the microbiome associated with a biological sample.

Performing the sequencing analysis operation S124 with identification of microbiome-derived sequences can include mapping of sequence data from sample processing to a subject reference genome (e.g., provided by the Genome Reference Consortium), in order to remove subject genome-derived sequences. Unidentified sequences remaining after mapping of sequence data to the subject reference genome can then be further clustered into operational taxonomic units (OTUs) based upon sequence similarity and/or reference-based approaches (e.g., using VAMPS, using MG-RAST, using QIIME databases), aligned (e.g., using a genome hashing approach, using a Needleman-Wunsch algorithm, using a Smith-Waterman algorithm), and mapped to reference bacterial genomes (e.g., provided by the National Center for Biotechnology Information), using an alignment algorithm (e.g., Basic Local Alignment Search Tool, FPGA accelerated alignment tool, BWT-indexing with BWA, BWT-indexing with SOAP, BWT-indexing with Bowtie, etc.). Mapping of unidentified sequences can additionally or alternatively include mapping to reference archaeal genomes, viral genomes and/or eukaryotic genomes. Furthermore, mapping of taxa can be performed in relation to existing databases, and/or in relation to custom-generated databases.

Additionally or alternatively, in relation to generating a microbiome functional diversity dataset, Block S120 can include extracting candidate features associated with functional aspects of one or more microbiome components of the aggregate set of biological samples S127, as indicated in the microbiome composition dataset. Extracting candidate functional features can include identifying functional features associated with one or more of: prokaryotic clusters of orthologous groups of proteins (COGs); eukaryotic clusters of orthologous groups of proteins (KOGs); any other suitable type of gene product; an RNA processing and modification functional classification; a chromatin structure and dynamics functional classification; an energy production and conversion functional classification; a cell cycle control and mitosis functional classification; an amino acid metabolism and transport functional classification; a nucleotide metabolism and transport functional classification; a carbohydrate metabolism and transport functional classification; a coenzyme metabolism functional classification; a lipid metabolism functional classification; a translation functional classification; a transcription functional classification; a replication and repair functional classification; a cell wall/membrane/envelop biogenesis functional classification; a cell motility functional classification; a post-translational modification, protein turnover, and chaperone functions functional classification; an inorganic ion transport and metabolism functional classification; a secondary metabolites biosynthesis, transport and catabolism functional classification; a signal transduction functional classification; an intracellular trafficking and secretion functional classification; a nuclear structure functional classification; a cytoskeleton functional classification; a general functional prediction only functional classification; and a function unknown functional classification; and any other suitable functional classification.

Additionally or alternatively, extracting candidate functional features in Block S127 can include identifying functional features associated with one or more of: systems information (e.g., pathway maps for cellular and organismal functions, modules or functional units of genes, hierarchical classifications of biological entities); genomic information (e.g., complete genomes, genes and proteins in the complete genomes, orthologous groups of genes in the complete genomes); chemical information (e.g., chemical compounds and glycans, chemical reactions, enzyme nomenclature); health information (e.g., human diseases, approved drugs, crude drugs and health-related substances); metabolism pathway maps; genetic information processing (e.g., transcription, translation, replication and repair, etc.) pathway maps; environmental information processing (e.g., membrane transport, signal transduction, etc.) pathway maps; cellular processes (e.g., cell growth, cell death, cell membrane functions, etc.) pathway maps; organismal systems (e.g., immune system, endocrine system, nervous system, etc.) pathway maps; human disease pathway maps; drug development pathway maps; and any other suitable pathway map.

In extracting candidate functional features, Block S127 can comprise performing a search of one or more databases, such as the Kyoto Encyclopedia of Genes and Genomes (KEGG) and/or the Clusters of Orthologous Groups (COGs) database managed by the National Center for Biotechnology Information (NCBI). Searching can be performed based upon results of generation of the microbiome composition dataset from one or more of the set of aggregate biological samples and/or sequencing of material from the set of samples. In more detail, Block S127 can include implementation of a data-oriented entry point to a KEGG database including one or more of a KEGG pathway tool, a KEGG BRITE tool, a KEGG module tool, a KEGG ORTHOLOGY (KO) tool, a KEGG genome tool, a KEGG genes tool, a KEGG compound tool, a KEGG glycan tool, a KEGG reaction tool, a KEGG disease tool, a KEGG drug tool, a KEGG medicus tool, Searching can additionally or alternatively be performed according to any other suitable filters. Additionally or alternatively, Block S127 can include implementation of an organism-specific entry point to a KEGG database including a KEGG organisms tool. Additionally or alternatively, Block S127 can include implementation of an analysis tool including one or more of: a KEGG mapper tool that maps KEGG pathway, BRITE, or module data; a KEGG atlas tool for exploring KEGG global maps, a BlastKOALA tool for genome annotation and KEGG mapping, a BLAST/FASTA sequence similarity search tool, and a SIMCOMP chemical structure similarity search tool. In specific examples, Block S127 can include extracting candidate functional features, based on the microbiome composition dataset, from a KEGG database resource and a COG database resource; however, Block S127 can comprise extracting candidate functional features in any other suitable manner. For instance, Block S127 can include extracting candidate functional features, including functional features derived from a Gene Ontology functional classification, and/or any other suitable features.

In one example, a taxonomic group can include one or more bacteria and their corresponding reference sequences. A sequence read can be assigned based on the alignment to a taxonomic group when the sequence read aligns to a reference sequence of the taxonomic group. A functional group can correspond to one or more genes labeled as having a similar function. Thus, a functional group can be represented by reference sequences of the genes in the functional group, where the reference sequences of a particular gene can correspond to various bacteria. The taxonomic and functional groups can collectively be referred to as sequence groups, as each group includes one or more reference sequences that represent the group. A taxonomic group of multiple bacteria can be represented by multiple reference sequence, e.g., one reference sequence per bacteria species in the taxonomic group. Embodiments can use the degree of alignment of a sequence read to multiple reference sequences to determine which sequence group to assign the sequence read based on the alignment.

1.2.1 Examples and Variations: Sequence Group Corresponds to Taxonomic Group

A taxonomic group can correspond to any set of one or more reference sequences for one or more loci (e.g., genes) that represent the taxonomic group. Any given level of a taxonomic hierarchy would include a plurality of taxonomic groups. For instance, a reference sequence in the one group at the genus level can be in another group at the family level.

The RAV can correspond to the proportion of reads assigned to a particular taxonomic group. The proportion can be relative to various denominator values, e.g., relative to all of the sequence reads, relative to all assigned to at least one group (taxonomic or functional), or all assigned to for a given level in the hierarchy. The alignment can be implemented in any manner that can assign a sequence read to a particular taxonomic group.

For example, based on the mappings to the reference sequence(s) in the 16S region, a taxonomic group with the best match for the alignment can be identified. The RAV can then be determined for that taxonomic group using the number of sequence reads (or votes of sequence reads) for a particular sequence group divided by the number of sequence reads identified as being bacterial, which may be for a specific region or even for a given level of a hierarchy.

1.2.2 Examples and Variations: Sequence Group Corresponds to Functional Group or Gene Instead of or in addition to determining a count of the sequence reads that correspond to a particular taxonomic group, embodiments can use a count of a number of sequence reads that correspond to a particular gene or a collection of genes having an annotation of a particular function, where the collection is called a functional group. The RAV can be determined in a similar manner as for a taxonomic group. For example, functional group can include a plurality of reference sequences corresponding to one or more genes of the functional group. Reference sequences of multiple bacteria for a same gene can correspond to a same functional group. Then, to determine the RAV, the number of sequence reads assigned to the functional group can be used to determine a proportion for the functional group.

The use of a function group, which may include a single gene, can help to identify situations where there is a small change (e.g., increase) in many taxonomic groups such that the change is too small to be statistically significant. But, the changes may all be for a same gene or set of genes of a same functional group, and thus the change for that functional group can be statistically significant, even though the changes for the taxonomic groups may not be significant. The reverse can be true of a taxonomic group being more predictive than a particular functional group, e.g., when a single taxonomic group includes many genes that have change by a relatively small amount.

As an example, if to taxonomic groups increase by 10%, the statistical power to discriminate between the two groups may be low when each taxonomic group is analyzed individually. But, if the increase is all for genes(s) of a same functional group, then the increase would be 100%, or a doubling of the proportion for that taxonomic group. This large increase would have a much larger statistical power for discriminating between the two groups. Thus, the functional group can act to provide a sum of small changes for various taxonomic groups. And, small changes for various functional groups, which happen to all be on a same taxonomic group, can sum to provide high statistical power for that particular taxonomic group.

The taxonomic groups and functional groups can supplement each other as the information can be orthogonal, or at least partially orthogonal as there still may be some relationship between the RAVs of each group. For example, the RAVs of one or more taxonomic groups and functional groups can be used together as multiple features of a feature vector, which is analyzed to provide a diagnosis, as is described herein. For instance, the feature vector can be compared to a disease signature as part of a characterization model.

1.2.3 Examples and Variations: Pipeline for Taxonomic Groups

Embodiments can provide a bioinformatics pipeline that taxonomically annotates the microorganisms present in a sample. The example annotation pipeline can comprise the following procedures.

In a first block, the samples can be identified and the sequence data can be loaded. For example, the pipeline can begin with demultiplexed fastq files (or other suitable files) that are the product of pair-end sequencing of amplicons (e.g., of the V4 region of the 16S gene). All samples can be identified for a given input sequencing file, and the corresponding fastq files can be obtained from the fastq repository server and loaded into the pipeline.

In a second block, the reads can be filtered. For example, a global quality filtering of reads in the fastq files can accept reads with a global Q-score>30. In one implementation, for each read, the per-position Q-scores are averaged, and if the average is equal or higher than 30, then the read is accepted, else the read is discarded, as is its paired read.

In a third block, primers can be identified and removed. In one embodiment, only forward reads that contain the forward primer and reverse reads that contain the reverse primer (allowing annealing of primers with up to 5 mismatches or other number of mismatches) are further considered. Primers and any sequences 5' to them are removed from the reads. The 125 bp (or other suitable number) towards the 3' of the forward primer are considered from the forward reads, and only 124 bp (or other suitable number) towards the 3' of the reverse primer are considered for the reverse reads. All processed forward reads that are <125 bp and reverse reads that are <124 bp are eliminated from further processing as are their paired reads.

In a fourth block, the forward and reverse reads can be written to files (e.g., FASTA files). For example, the forward and reverse reads that remained paired can be used to generate files that contain 125 bp from the forward read, concatenated to 124 bp from the reverse read (in the reverse complement direction).

In a fifth block, the sequence reads can be clustered, e.g., to identify chimeric sequences or determine a consensus sequence for a bacterium. For example, the sequences in the files can be subjected to clustering using the Swarm algorithm with a distance of 1. This treatment allows the generation of cluster composed of a central biological entity, surrounded by sequences which are 1 mutation away from the biological entity, which are less abundant and the result of the normal base calling error associated to high throughput sequencing. Singletons are removed from further analyses. In the remaining clusters, the most abundant sequence per cluster is then used as the representative and assigned the counts of all members in the cluster.

In a sixth block, chimeric sequences can be removed. For example, amplification of gene superfamilies can produce the formation of chimeric DNA sequences. These result from a partial PCR product from one member of the superfamily that anneals and extends over a different member of the superfamily in a subsequent cycle of PCR. In order to remove chimeric DNA sequences, some embodiments can use the VSEARCH chimera detection algorithm with the de novo option and standard parameters. This algorithm uses abundance of PCR products to identify reference "real" sequences as those most abundant, and chimeric products as those less abundant and displaying local similarity to two or more of the reference sequences. All chimeric sequences can be removed from further analysis.

In a seventh block, taxonomy annotation can be assigned to sequences using sequence identity searches. To assign taxonomy to the sequences that have passed all filters above, some embodiments can perform identity searches against a database that contains bacterial strains (e.g., reference sequences) annotated to phylum, class, order, family, genus and species level, or any other taxonomic levels. The most specific level of taxonomy annotation for a sequence can be kept, given that higher order taxonomy designations for a lower level taxonomy level can be inferred. The sequence identity search can be performed using the algorithm VSEARCH with parameters (maxaccepts=0, maxrejects=0, id=1) that allow an exhaustive exploration of the reference database used. Decreasing values of sequence identity can be used to assign sequences to different taxonomic groups: >97% sequence identity for assigning to a species, >95% sequence identity for assigning to a genus, >90% for assigning to family, >85% for assigning to order, >80% for assigning to class, and >77% for assigning to phylum.

In an eighth block, relative abundances of each taxa can be estimated and output to a database. For example, once all sequences have been used to identify sequences in the reference database, relative abundance per taxa can be determined by dividing the count of all sequences that are assigned to the same taxonomic group by the total number of reads that passed filters, e.g., were assigned. Results can be uploaded to database tables that are used as repository for the taxonomic annotation data.

1.2.4 Examples and Variations: Pipeline for Functional Groups

For functional groups, the process can proceed as follows.

In a first step, sample OTUs (Operational Taxonomic Units) can be found. This may occur after the sixth block from above. After the sixth block above, sequences can be clustered, e.g., based on sequence identity (e.g., 97% sequence identity).

In a second step, a taxonomy can be assigned, e.g., by comparing OTUs with reference sequences of known taxonomy. The comparison can be based on sequence identity (e.g., 97%).

In a third step, taxonomic abundance can be adjusted for 16S copy number, or whatever genomic regions may be analyzed. Different species may have different number of copies of the 16S gene, so those possessing higher number of copies will have more 16S material for PCR amplification at same number of cells than other species. Therefore, abundance can be normalized by adjusting the number of 16S copies.

In a fourth step, a pre-computed genomic lookup table can be used to relate taxonomy to functions, and amount of function. For example, a pre-computed genomic lookup table that shows the number of genes for important KEGG or COG functional categories per taxonomic group can be used to estimate the abundance of those functional categories based on the normalized 16S abundance data.

Upon identification of represented groups of microorganisms of the microbiome associated with a biological sample and/or identification of candidate functional aspects (e.g., functions associated with the microbiome components of the biological samples), generating features derived from compositional and/or functional aspects of the microbiome associated with the aggregate set of biological samples can be performed.

In one variation, generating features can include generating features derived from multilocus sequence typing (MLST), which can be performed experimentally at any stage in relation to implementation of the methods 100, 200, in order to identify markers useful for characterization in subsequent blocks of the method 100. Additionally or alternatively, generating features can include generating features that describe the presence or absence of certain taxonomic groups of microorganisms, and/or ratios between exhibited taxonomic groups of microorganisms. Additionally or alternatively, generating features can include generating features describing one or more of: quantities of represented taxonomic groups, networks of represented taxonomic groups, correlations in representation of different taxonomic groups, interactions between different taxonomic groups, products produced by different taxonomic groups, interactions between products produced by different taxonomic groups, ratios between dead and alive microorganisms (e.g., for different represented taxonomic groups, based upon analysis of RNAs), phylogenetic distance (e.g., in terms of Kantorovich-Rubinstein distances, Wasserstein distances etc.), any other suitable taxonomic group-related feature(s), any other suitable genetic or functional feature(s).

Additionally or alternatively, generating features can include generating features describing relative abundance of different microorganism groups, for instance, using a sparCC approach, using Genome Relative Abundance and Average size (GAAS) approach and/or using a Genome Relative Abundance using Mixture Model theory (GRAMMy) approach that uses sequence-similarity data to perform a maximum likelihood estimation of the relative abundance of one or more groups of microorganisms. Additionally or alternatively, generating features can include generating statistical measures of taxonomic variation, as derived from abundance metrics. Additionally or alternatively, generating features can include generating features derived from relative abundance factors (e.g., in relation to changes in abundance of a taxon, which affects abundance of other taxa). Additionally or alternatively, generating features can include generation of qualitative features describing presence of one or more taxonomic groups, in isolation and/or in combination. Additionally or alternatively, generating features can include generation of features related to genetic markers (e.g., representative 16S, 18S, and/or ITS sequences) characterizing microorganisms of the microbiome associated with a biological sample. Additionally or alternatively, generating features can include generation of features related to functional associations of specific genes and/or organisms having the specific genes. Additionally or alternatively, generating features can include generation of features related to pathogenicity of a taxon and/or products attributed to a taxon. Block S120 can, however, include generation of any other suitable feature(s) derived from sequencing and mapping of nucleic acids of a biological sample. For instance, the feature(s) can be combinatory (e.g., involving pairs, triplets), correlative (e.g., related to correlations between different features), and/or related to changes in features (i.e., temporal changes, changes across sample sites, spatial changes, etc.). Features can, however, be generated in any other suitable manner in Block S120.

1.3 First Method: Supplementary Data

Block S130 recites: receiving a supplementary dataset, associated with at least a subset of the population of subjects, wherein the supplementary dataset is informative of characteristics associated with the mental health associated condition. The supplementary dataset can thus be informative of presence of the condition within the population of subjects. Block S130 functions to acquire additional data associated with one or more subjects of the set of subjects, which can be used to train and/or validate the characterization processes performed in Block S140. In Block S130, the supplementary dataset preferably includes survey-derived data, but can additionally or alternatively include any one or more of: contextual data derived from sensors, medical data (e.g., current and historical medical data associated with a mental health associated condition), and any other suitable type of data. In variations of Block S130 including reception of survey-derived data, the survey-derived data preferably provides physiological, demographic, and behavioral information in association with a subject. Physiological information can include information related to physiological features (e.g., height, weight, body mass index, body fat percent, body hair level, etc.). Demographic information can include information related to demographic features (e.g., gender, age, ethnicity, marital status, number of siblings, socioeconomic status, sexual orientation, etc.). Behavioral information can include information related to one or more of: health conditions (e.g., health and disease states), living situations (e.g., living alone, living with pets, living with a significant other, living with children, etc.), dietary habits (e.g., omnivorous, vegetarian, vegan, sugar consumption, acid consumption, etc.), behavioral tendencies (e.g., levels of physical activity, drug use, alcohol use, etc.), different levels of mobility (e.g., related to distance traveled within a given time period), different levels of sexual activity (e.g., related to numbers of partners and sexual orientation), and any other suitable behavioral information. Survey-derived data can include quantitative data and/or qualitative data that can be converted to quantitative data (e.g., using scales of severity, mapping of qualitative responses to quantified scores, etc.).

In facilitating reception of survey-derived data, Block S130 can include providing one or more surveys to a subject of the population of subjects, or to an entity associated with a subject of the population of subjects. Surveys can be provided in person (e.g., in coordination with sample provision and reception from a subject), electronically (e.g., during account setup by a subject, at an application executing at an electronic device of a subject, at a web application accessible through an internet connection, etc.), and/or in any other suitable manner.

Additionally or alternatively, portions of the supplementary dataset received in Block S130 can be derived from sensors associated with the subject(s) (e.g., sensors of wearable computing devices, sensors of mobile devices, biometric sensors associated with the user, etc.). As such, Block S130 can include receiving one or more of: physical activity- or physical action-related data (e.g., accelerometer and gyroscope data from a mobile device or wearable electronic device of a subject), environmental data (e.g., temperature data, elevation data, climate data, light parameter data, etc.), patient nutrition or diet-related data (e.g., data from food establishment check-ins, data from spectrophotometric analysis, etc.), biometric data (e.g., data recorded through sensors within the patient's mobile computing device, data recorded through a wearable or other peripheral device in communication with the patient's mobile computing device), location data (e.g., using GPS elements), and any other suitable data. Additionally or alternatively, portions of the supplementary dataset can be derived from medical record data and/or clinical data of the subject(s). As such, portions of the supplementary dataset can be derived from one or more electronic health records (EHRs) of the subject(s).

Additionally or alternatively, the supplementary dataset of Block S130 can include any other suitable diagnostic information (e.g., clinical diagnosis information), which can be combined with analyses derived from features to support characterization of subjects in subsequent blocks of the method 100. For instance, information derived from a colonoscopy, biopsy, blood test, diagnostic imaging, survey-related information, and any other suitable test can be used to supplement Block S130.

1.4 First Method: Characterizations of the Mental Health Associated Condition

Block S140 recites: transforming the supplementary dataset and features extracted from at least one of the microbiome composition dataset and the microbiome functional diversity dataset into a characterization model of the mental health associated condition. Block S140 functions to perform a characterization process for identifying features and/or feature combinations that can be used to characterize subjects or groups with the mental health associated condition based upon their microbiome composition and/or functional features. Additionally or alternatively, the characterization process can be used as a diagnostic tool that can characterize a subject (e.g., in terms of behavioral traits, in terms of medical conditions, in terms of demographic traits, etc.) based upon their microbiome composition and/or functional features, in relation to other health condition states, behavioral traits, medical conditions, demographic traits, and/or any other suitable traits. Such characterization can then be used to suggest or provide personalized therapies by way of the therapy model of Block S150.

In performing the characterization process, Block S140 can use computational methods (e.g., statistical methods, machine learning methods, artificial intelligence methods, bioinformatics methods, etc.) to characterize a subject as exhibiting features characteristic of a group of subjects with the mental health associated condition.

In one variation, characterization can be based upon features derived from a statistical analysis (e.g., an analysis of probability distributions) of similarities and/or differences between a first group of subjects exhibiting a target state (e.g., a health condition state) associated with the mental health associated condition, and a second group of subjects not exhibiting the target state (e.g., a "normal" state) associated with the mental health associated condition. In implementing this variation, one or more of a Kolmogorov-Smirnov (KS) test, a permutation test, a Cramér-von Mises test, and any other statistical test (e.g., t-test, Welch's t-test, z-test, chi-squared test, test associated with distributions, etc.) can be used. In particular, one or more such statistical hypothesis tests can be used to assess a set of features having varying degrees of abundance in (or variations across) a first group of subjects exhibiting a target state (i.e., an adverse state) associated with the mental health associated condition and a second group of subjects not exhibiting the target state (i.e., having a normal state) associated with the mental health associated condition. In more detail, the set of features assessed can be constrained based upon percent abundance and/or any other suitable parameter pertaining to diversity in association with the first group of subjects and the second group of subjects, in order to increase or decrease confidence in the characterization. In a specific implementation of this example, a feature can be derived from a taxon of microorganism and/or presence of a functional feature that is abundant in a certain percentage of subjects of the first group and subjects of the second group, wherein a relative abundance of the taxon between the first group of subjects and the second group of subjects can be determined from one or more of a KS test or a Welch's t-test (e.g., a t-test with a log normal transformation), with an indication of significance (e.g., in terms of p-value). Thus, an output of Block S140 can comprise a normalized relative abundance value (e.g., 25% greater abundance of a taxon-derived feature and/or a functional feature in sick subjects vs. healthy subjects) with an indication of significance (e.g., a p-value of 0.0013). Variations of feature generation can additionally or alternatively implement or be derived from functional features or metadata features (e.g., non-bacterial markers).

In variations and examples, characterization can use the relative abundance values (RAVs) for populations of subjects that have a disease (condition population) and that do not have the disease (control population). If the distribution of RAVs of a particular sequence group for the condition population is statistically different than the distribution of RAVs for the control population, then the particular sequence group can be identified for including in a disease signature. Since the two populations have different distributions, the RAV for a new sample for a sequence group in the disease signature can be used to classify (e.g., determine a probability) of whether the sample does or does not have the disease. The classification can also be used to determine a treatment, as is described herein. A discrimination level can be used to identify sequence groups that have a high predictive value. Thus, embodiment can filter out taxonomic groups and/or functional groups that are not very accurate for providing a diagnosis.

Once RAVs of a sequence group have been determined for the control and condition populations, various statistical tests can be used to determine the statistical power of the sequence group for discriminating between disease (condition) and no disease (control). In one embodiment, the Kolmogorov-Smirnov (KS) test can be used to provide a probability value (p-value) that the two distributions are actually identical. The smaller the p-value the greater the probability to correctly identify which population a sample belongs. The larger the separation in the mean values between the two populations generally results in a smaller p-value (an example of a discrimination level). Other tests for comparing distributions can be used. The Welch's t-test presumes that the distributions are Gaussian, which is not necessarily true for a particular sequence group. The KS test, as it is a non-parametric test, is well suited for comparing distributions of taxa or functions for which the probability distributions are unknown.

The distribution of the RAVs for the control and condition populations can be analyzed to identify sequence groups with a large separation between the two distributions. The separation can be measured as a p-value (See example section). For example, the relative abundance values for the control population may have a distribution peaked at a first value with a certain width and decay for the distribution. And, the condition population can have another distribution that is peaked a second value that is statistically different than the first value. In such an instance, an abundance value of a control sample has a lower probability to be within the distribution of abundance values encountered for the condition samples. The larger the separation between the two distributions, the more accurate the discrimination is for determining whether a given sample belongs to the control population or the condition population. As is discussed later, the distributions can be used to determine a probability for an RAV as being in the control population and determine a probability for the RAV being in the condition population, where sequence groups associated with the largest percentage difference between two means have the smallest p-value, signifying a greater separation between the two populations.

In performing the characterization process, Block S140 can additionally or alternatively transform input data from at least one of the microbiome composition dataset and microbiome functional diversity dataset into feature vectors that can be tested for efficacy in predicting characterizations of the population of subjects. Data from the supplementary dataset can be used to inform characterizations of the mental health associated condition, wherein the characterization process is trained with a training dataset of candidate features and candidate classifications to identify features and/or feature combinations that have high degrees (or low degrees) of predictive power in accurately predicting a classification. As such, refinement of the characterization process with the training dataset identifies feature sets (e.g., of subject features, of combinations of features) having high correlation with presence of the mental health associated condition.

In variations, feature vectors effective in predicting classifications of the characterization process can include features related to one or more of: microbiome diversity metrics (e.g., in relation to distribution across taxonomic groups, in relation to distribution across archaeal, bacterial, viral, and/or eukaryotic groups), presence of taxonomic groups in one's microbiome, representation of specific genetic sequences (e.g., 16S sequences) in one's microbiome, relative abundance of taxonomic groups in one's microbiome, microbiome resilience metrics (e.g., in response to a perturbation determined from the supplementary dataset), abundance of genes that encode proteins or RNAs with given functions (enzymes, transporters, proteins from the immune system, hormones, interference RNAs, etc.) and any other suitable features derived from the microbiome composition dataset, the microbiome functional diversity dataset (e.g., COG-derived features, KEGG derived features, other functional features, etc.), and/or the supplementary dataset.

Additionally, combinations of features can be used in a feature vector, wherein features can be grouped and/or weighted in providing a combined feature as part of a feature set. For example, one feature or feature set can include a weighted composite of the number of represented classes of bacteria in one's microbiome, presence of a specific genus of bacteria in one's microbiome, representation of a specific 16S sequence in one's microbiome, and relative abundance of a first phylum over a second phylum of bacteria. However, the feature vectors can additionally or alternatively be determined in any other suitable manner.

In examples of Block S140, assuming sequencing has occurred at a sufficient depth, one can quantify the number of reads for sequences indicative of the presence of a feature (e.g., features described in Sections 1.4.1-1.4.7 below), thereby allowing one to set a value for an estimated amount of one of the criteria. The number of reads or other measures of amount of one of the features can be provided as an absolute or relative value. An example of an absolute value is the number of reads of 16S RNA coding sequence reads that map to a specific genus. Alternatively, relative amounts can be determined. An exemplary relative amount calculation is to determine the amount of 16S RNA coding sequence reads for a particular taxon (e.g., genus, family, order, class, or phylum) relative to the total number of 16S RNA coding sequence reads assigned to the domain. A value indicative of amount of a feature in the sample can then be compared to a cut-off value or a probability distribution in a disease signature for a mental health associated condition. For example, if the disease signature indicates that a relative amount of feature #1 of 50% or more of all features possible at that level indicates the likelihood of a mental health associated condition, then quantification of gene sequences associated with feature #1 less than 50% in a sample would indicate a higher likelihood of healthy (or at least not that specific mental health associated condition) and alternatively, quantification of gene sequences associated with feature #1 more than 50% in a sample would indicate a higher likelihood of disease.

In examples, the taxonomic groups and/or functional groups can be referred to as features, or as sequence groups in the context of determining an amount of sequence reads corresponding to a particular group (feature). In examples, scoring of a particular bacteria or genetic pathway can be determined according to a comparison of an abundance value to one or more reference (calibration) abundance values for known samples, e.g., where a detected abundance value less than a certain value is associated with the mental health associated condition in question and above the certain value is scored as associated with healthy, or vice versa depending on the particular criterion. The scoring for various bacteria or genetic pathways can be combined to provide a classification for a subject. Furthermore, in the examples, the comparison of an abundance value to one or more reference abundance values can include a comparison to a cutoff value determined from the one or more reference values. Such cutoff value(s) can be part of a decision tree or a clustering technique (where a cutoff value is used to determine which cluster the abundance value(s) belong) that are determined using the reference abundance values. The comparison can include intermediate determination of other values, (e.g., probability values). The comparison can also include a comparison of an abundance value to a probability distribution of the reference abundance values, and thus a comparison to probability values.

In some embodiments, certain samples may not exhibit any presence of a particular taxonomic group, or at least not a presence above a relatively low threshold (i.e., a threshold below either of the two distributions for the control and condition population). Thus, a particular sequence group may be prevalent in the population, e.g., more than 30% of the population may have the taxonomic group. Another sequence group may be less prevalent in the population, e.g., showing up in only 5% of the population. The prevalence (e.g., percentage of population) of a certain sequence group can provide information as to how likely the sequence group may be used to determine a diagnosis.

In such an example, the sequence group can be used to determine a status of the condition (e.g., diagnose for the condition) when the subject falls within the 30%. But, when the subject does not fall within the 30%, such that the taxonomic group is simply not present, the particular taxonomic group may not be helpful in determining a diagnosis of the subject. Thus, whether a particular taxonomic group or functional group is useful in diagnosing a particular subject can be dependent on whether nucleic acid molecules corresponding to the sequence group are actually sequenced.

Accordingly, a disease signature can include more sequence groups that are used for a given subject. As an example, the disease signature can include too sequence groups, but only 60 of sequence groups may be detected in a sample. The classification of the subject (including any probability for being in the application) would be determined based on the 60 sequence groups.

In relation to generation of the characterization model, the sequence groups with high discrimination levels (e.g., low p-values) for a given disease can be identified and used as part of a characterization model, e.g., which uses a disease signature to determine a probability of a subject having the disease. The disease signature can include a set of sequence groups as well as discriminating criteria (e.g., cutoff values and/or probability distributions) used to provide a classification of the subject. The classification can be binary (e.g., disease or non-disease) or have more classifications (e.g., probability values for having the disease or not having the disease). Which sequence groups of the disease signature that are used in making a classification be dependent on the specific sequence reads obtained, e.g., a sequence group would not be used if no sequence reads were assigned to that sequence group. In some embodiments, a separate characterization model can be determined for different populations, e.g., by geography where the subject is currently residing (e.g., country, region, or continent), the generic history of the subject (e.g., ethnicity), or other factors.

1.4.0 Selection of Sequence Groups. Discrimination Criteria Sequence Groups. And Use of Sequence Groups As mentioned above, sequence groups having at least a specified discrimination level can be selected for inclusion in the characterization model. In various embodiments, the specified discrimination level can be an absolute level (e.g., having a p-value below a specified value), a percentage (e.g., being in the top 10% of discriminating levels), or a specified number of the top discrimination levels (e.g., the top too discriminating levels). In some embodiments, the characterization model can include a network graph, where each node in a graph corresponds to a sequence group having at least a specified discrimination level.

The sequence groups used in a disease signature of a characterization model can also be selected based on other factors. For example, a particular sequence group may only be detected in a certain percentage of the population, referred to as a coverage percentage. An ideal sequence group would be detected in a high percentage of the population and have a high discriminating level (e.g., a low p-value). A minimum percentage may be required before adding the sequence group to the characterization model for a particular disease. The minimum percentage can vary based on the accompanying discriminating level. For instance, a lower coverage percentage may be tolerated if the discriminating level is higher. As a further example, 95% of the patients with a condition may be classified with one or a combination of a few sequence groups, and the 5% remaining can be explained based on one sequence group, which relates to the orthogonality or overlap between the coverage of sequence groups. Thus, a sequence group that provides discriminating power for 5% of the diseased individuals may be valuable.

Another factor for determining which sequence to include in a disease signature of the characterization model is the overlap in the subjects exhibiting the sequence groups of a disease signature. For example, two sequence groups can both have a high coverage percentage, but sequence groups may cover the exact same subjects. Thus, adding one of the sequence groups does increase the overall coverage of the disease signature. In such a situation, the two sequence groups can be considered parallel to each other. Another sequence group can be selected to add to the characterization model based on the sequence group covering different subjects than other sequence groups already in the characterization model. Such a sequence group can be considered orthogonal to the already existing sequence groups in the characterization model.

As examples, selecting a sequence group may consider the following factors. A taxa may appear in 100% of healthy individuals and in 100% of diseased individuals, but where the distributions are so close in both groups, that knowing the relative abundance of that taxa only allows to catalogue a few individuals as diseased or healthy (i.e. it has a low discriminating level). Whereas, a taxa that appears in only 20% of healthy individuals and 30% of diseased individuals can have distributions of relative abundance that are so different from one another, it allows to catalogue 20% of healthy individuals and 30% of diseased individuals (i.e. it has a high discriminating level).

In some embodiments, machine learning techniques can allow the automatic identification of the best combination of features (e.g., sequence groups). For instance, a Principal Component Analysis can reduce the number of features used for classification to only those that are the most orthogonal to each other and can explain most of the variance in the data. The same is true for a network theory approach, where one can create multiple distance metrics based on different features and evaluate which distance metric is the one that best separates diseased from healthy individuals.

The discrimination criteria for the sequence groups included in the disease signature of a characterization model can be determined based on the condition distributions and the control distributions for the disease. For example, a discrimination criterion for a sequence group can be a cutoff value that is between the mean values for the two distributions. As another example, discrimination criteria for a sequence group can include probability distributions for the control and condition populations. The probability distributions can be determined in a separate manner from the process of determining the discrimination level.

The probability distributions can be determined based on the distribution of RAVs for the two populations. The mean values (or other average or median) for the two populations can be used to center the peaks of the two probability distributions. For example, if the mean RAV of the condition population is 20% (or 0.2), then the probability distribution for the condition population can have its peak at 20%. The width or other shape parameters (e.g., the decay) can also be determined based on the distribution of RAVs for the condition population. The same can be done for the control population.

The sequence groups included in the disease signature of the characterization can be used to classify a new subject. The sequence groups can be considered features of the feature vector, or the RAVs of the sequence groups considered as features of a feature vector, where the feature vector can be compared to the discriminating criteria of the disease signature. For instance, the RAVs of the sequence groups for the new subject can be compared to the probability distributions for each sequence group of the disease signature. If an RAV is zero or nearly zero, then the sequence group may be skipped and not used in the classification.

The RAVs for sequence groups that are exhibited in the new subject can be used to determine the classification. For example, the result (e.g., a probability value) for each exhibited sequence group can be combined to arrive at the final classification. As another example, clustering of the RAVs can be performed, and the clusters can be used to determine a classification of a condition.

Figure 4:
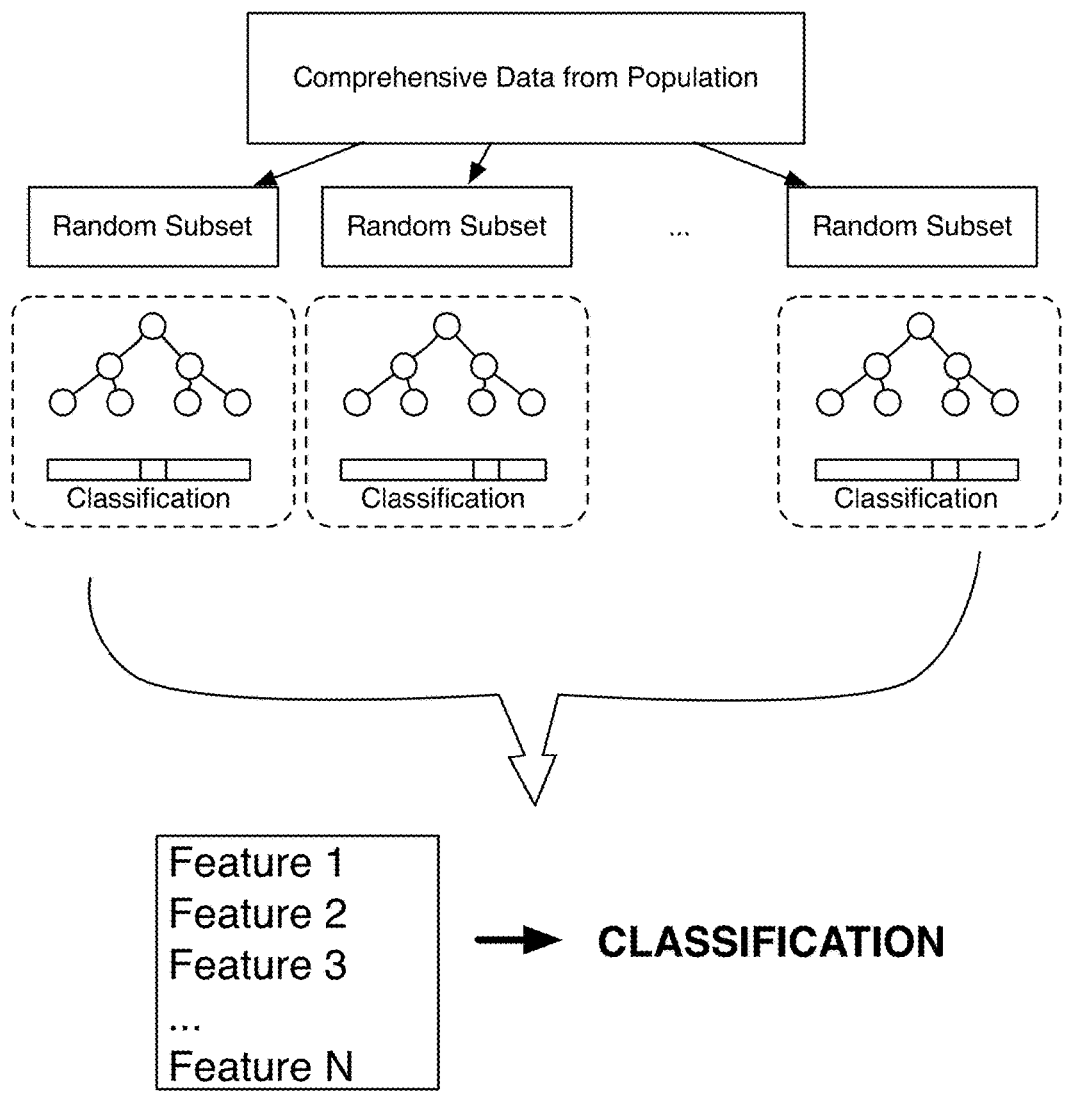
FIG. 4 depicts a variation of a process for generation of a model in an embodiment of a method and system for generating microbiome-derived diagnostics and therapeutics.

As shown in FIG. 4, in one such alternative variation of Block S140, the characterization process can be generated and trained according to a random forest predictor (RFP) algorithm that combines bagging (i.e., bootstrap aggregation) and selection of random sets of features from a training dataset to construct a set of decision trees, T, associated with the random sets of features. In using a random forest algorithm, N cases from the set of decision trees are sampled at random with replacement to create a subset of decision trees, and for each node, m prediction features are selected from all of the prediction features for assessment. The prediction feature that provides the best split at the node (e.g., according to an objective function) is used to perform the split (e.g., as a bifurcation at the node, as a trifurcation at the node). By sampling many times from a large dataset, the strength of the characterization process, in identifying features that are strong in predicting classifications can be increased substantially. In this variation, measures to prevent bias (e.g., sampling bias) and/or account for an amount of bias can be included during processing to increase robustness of the model.

1.4.1 Acid Reflux/Gastroesophageal Reflux Disease (GERD) Characterization

In one implementation, a characterization process of Block S140 based upon statistical analyses can identify the sets of features that have the highest correlations with GERD, for which one or more therapies would have a positive effect, based upon an algorithm trained and validated with a validation dataset derived from a subset of the population of subjects. In particular, GERD in this first variation is a gastrointestinal disorder characterized by exhibition of symptoms, as typically detected using one or more of: esophagogastroduodenoscopy (EGD), endoscopy, radiography (e.g., radiography with a barium swallow), biopsy, manometry, impedance monitoring, and pH monitoring. In the first variation, a set of features useful for diagnostics associated with GERD includes features derived from one or more of the following taxa: *Sarcina* (genus), *Blautia* (genus), *Terrisporobacter* (genus), *Faecalibacterium* (genus), *Moryella* (genus), *Lactobacillus* (genus), *Clostridium* (genus), *Odoribacter* (genus), *Thalassospira* (genus), *Barnesiella* (genus), *Subdoligranulum* (genus), *Bifidobacterium* (genus), *Anaerotruncus* (genus), *Streptococcus* (genus), *Parabacteroides* (genus), *Alistipes* (genus), *Erysipelatoclostridium* (genus), *Bacteroides* (genus), *Methanobrevibacter* (genus), *Phascolarctobacterium*, *Butyricimonas* (genus), Clostridiaceae (family), Lactobacillaceae (family), Ruminococcaceae (family), Rhodospirillaceae (family), Lachnospiraceae (family), Bifidobacteriaceae (family), Flavobacteriaceae (family), Rikenellaceae (family), Sutterellaceae (family), Bacteroidaceae (family), Peptostreptococcaceae (family), Veillonellaceae (family), Oscillospiraceae (family), Methanobacteriaceae (family), Prevotellaceae (family), Rhodospirillales (order), Bifidobacteriales (order), Flavobacteriales (order), Burkholderiales (order), Alphaproteobacteria (class), Flavobacteria (class), Betaproteobacteria (class), Methanobacteria (class), Bacteroidia (class), Proteobacteria (phylum), Euryarchaeota (phylum), Verrucomicrobia (phylum), and Bacteroidetes (phylum).

Additionally or alternatively, the set of features associated with GERD can be derived from one or more of the following taxa: Tenericutes (phylum), Bacilli (class), Erysipelotrichia (class), Mollicutes (class), Lactobacillales (order), Erysipelotrichales (order), Bifidobacteriales (order), Bacteroidaceae (family), Peptostreptococcaceae (family), Erisipelotrichaceae (family), Christensenellaceae (family), Bifidobacteriaceae (family), *Bacteroides* (genus), *Parabacteroides* (genus), *Ruminococcus* (genus), *Subdoligranulum* (genus), *Turicibacter* (genus), *Streptococcus thermophilus* (species), *Roseburia inulinivorans* (species), bacterium NLAE-zl-P430 (species), *Flavonifractor plautii* (species), *Faecalibacterium prausnitzii* (species), bacterium NLAE-zl-P562 (species), *Parabacteroides merdae* (species), *Parabacteroides distasonis* (species), *Collinsella aerofaciens* (species), and *Clostridiales* bacterium A2-162 (species), unclassified bacteria (no rank), Peptostreptococcaceae (no rank), environmental samples (no rank).

Additionally or alternatively, the set of features associated with GERD can be derived from one or more of: a cell motility KEGG L2 derived feature; a carbohydrate metabolism KEGG L2 derived feature; an environmental adaptation KEGG L2 derived feature; a signaling molecules and interaction KEGG L2 derived feature; a metabolism KEGG L2 derived feature; an energy metabolism KEGG L2 derived feature; a signal transduction KEGG L2 derived feature; a xenobiotics biodegradation and metabolism KEGG L2 derived feature; a translation KEGG L2 derived feature; a lipid metabolism KEGG L2 derived feature; a metabolism of other amino acids KEGG L2 derived feature; an immune system diseases KEGG L2 derived feature; a secretion system KEGG L3 derived feature; a selenocompound metabolism KEGG L3 derived feature; a fructose and mannose metabolism KEGG L3 derived feature; a bacterial chemotaxis KEGG L3 derived feature; an amino acid metabolism KEGG L3 derived feature; a plant-pathogen interaction KEGG L3 derived feature; a bacterial toxins KEGG L3 derived feature; a pyruvate metabolism KEGG L3 derived feature; a general function prediction KEGG L3 derived feature; a nitrogen metabolism KEGG L3 derived feature; a two-component system KEGG L3 derived feature; a ribosome biogenesis KEGG L3 derived feature; a propanoate metabolism KEGG L3 derived feature; a tuberculosis KEGG L3 derived feature; a fatty acid biosynthesis KEGG L3 derived feature; a oxidative phosphorylation KEGG L3 derived feature; a Glyoxylate and dicarboxylate metabolism KEGG L3 derived feature; an Alzheimer's disease KEGG L3 derived feature; a biotin metabolism KEGG L3 derived feature; a pentose phosphate pathway KEGG L3 derived feature; a galactose metabolism KEGG L3 derived feature; a methane metabolism KEGG L3 derived feature; a ribosome biogenesis in eukaryotes KEGG L3 derived feature; a bacterial secretion system KEGG L3 derived feature; a beta-Alanine metabolism KEGG L3 derived feature; a pentose and glucuronate interconversions KEGG L3 derived feature; a polyketide sugar unit biosynthesis KEGG L3 derived feature; a streptomycin biosynthesis KEGG L3 derived feature; a protein export KEGG L3 derived feature; an Aminoacyl-tRNA biosynthesis KEGG L3 derived feature; a chloroalkane and chloroalkene degradation KEGG L3 derived feature; a translation proteins KEGG L3 derived feature; a folate biosynthesis KEGG L3 derived feature; a phosphotransferase system KEGG L3 derived feature; an other transporters KEGG L3 derived feature; a glycerophospholipid metabolism KEGG L3 derived feature; a glycine, serine, and threonine metabolism KEGG L3 derived feature; a terpenoid backbone biosynthesis KEGG L3 derived feature; a riboflavin metabolism KEGG L3 derived feature; a vitamin metabolism KEGG L3 derived feature; a ribosome KEGG L3 derived feature; a homologous recombination KEGG L3 derived feature; a chromosome KEGG L3 derived feature; an inositol phosphate metabolism KEGG L3 derived feature; a naphthalene degradation KEGG L3 derived feature; a phosphatidylinositol signaling system KEGG L3 derived feature; and a taurine and hypotaurine metabolism KEGG L3 derived feature.

Thus, characterization of the subject comprises characterization of the subject as someone with acid reflux/GERD based upon detection of one or more of the above features, in a manner that is an alternative or supplemental to typical methods of diagnosis. In variations of the specific example, the set of features can, however, include any other suitable features useful for diagnostics.

1.4.2 AIDS Characterization

In another implementation, a characterization process of Block S140 based upon statistical analyses can identify the sets of features that have the highest correlations with acquired immune deficiency syndrome (AIDS), for which one or more therapies would have a positive effect, based upon an algorithm trained and validated with a validation dataset derived from a subset of the population of subjects. In particular, AIDS in this first variation is an immune disease characterized by immunodeficiency, as typically assessed based upon analysis of immune response materials (e.g., cells, antibodies, cytokines, etc.) and comparison to a given threshold level of a material. In the first variation, a set of features useful for diagnostics associated with AIDS includes features derived from one or more of the following taxa: Prevotellaceae (family), *Prevotella* (genus), *Megasphaera* (genus), Veillonellaceae (family), Erysipelotrichaceae (family), Erysipelotrichia (class), Erysipelotrichales (order), Bacteroidia (class), Bacteroidetes (phylum), Bacteroidetes/Chlorobi group (superphylum), Bacteroidales (order), Selenomonadales (order), Negativicutes (class), Lachnospiraceae (family), Flavobacteriia (class), Flavobacteriales (order), Flavobacteriaceae (family), *Clostridium* (genus), *Coprococcus* (genus), Porphyromonadaceae (family), *Eubacterium ramulus* (species), Oscillospiraceae (family), Acidaminococcaceae (family), *Lachnospira* (genus), *Barnesiella* (genus), *Phascolarctobacterium* (genus), *Parasutterella* (genus), *Parasutterella excrementihominis* (species), and *Eubacterium ramulus* (species).

Additionally or alternatively, the set of features associated with AIDS can be derived from one or more of: COG derived features, KEGG L2, L3, L4 derived features, and any other suitable functional features. In specific examples, such features can include one or more of: a neurodegenerative diseases KEGG L2 derived feature; a transcription KEGG L2 derived feature; a metabolism of cofactors and vitamins KEGG L2 derived feature; an endocrine system KEGG L2 derived feature; a cancers KEGG L2 derived feature; an amino acid metabolism KEGG L2 derived feature; a glycolysis/gluconeogenesis KEGG L3 derived feature; a streptomycin biosynthesis KEGG L3 derived feature; a restriction enzyme KEGG L3 derived feature; a fatty acid biosynthesis KEGG L3 derived feature; a PPAR signaling pathway KEGG L3 derived feature; a phosphotransferase system (PTS) KEGG L3 derived feature; a lipid metabolism KEGG L3 derived feature; an aminobenzoate degradation KEGG L3 derived feature; a pathways in cancer KEGG L3 derived feature; a mismatch repair KEGG L3 derived feature; a vitamin B6 metabolism KEGG L3 derived feature; a butirosin and neomycin biosynthesis KEGG L3 derived feature; a pantothenate and CoA biosynthesis KEGG L3 derived feature; an oxidative phosphorylation KEGG L3 derived feature; a zeatin biosynthesis KEGG L3 derived feature; an energy metabolism KEGG L3 derived feature; a limonene and pinene degradation KEGG L3 derived feature; a valine, leucine, and isoleucine biosynthesis KEGG L3 derived feature; a bacterial chemotaxis KEGG L3 derived feature; a homologous recombination KEGG L3 derived feature; a lipopolysaccharide biosynthesis proteins KEGG L3 derived feature; a transcription machinery KEGG L3 derived feature; and a selenocompound KEGG L3 derived feature.

Thus, characterization of the subject comprises characterization of the subject as someone with AIDS based upon detection of one or more of the above features, in a manner that is an alternative or supplemental to typical methods of diagnosis. In variations of the specific example, the set of features can, however, include any other suitable features useful for diagnostics.

1.4.3 Colorectal Cancer Characterization

In another implementation, a characterization process of Block S140 based upon statistical analyses can identify the sets of features that have the highest correlations with colorectal cancer, for which one or more therapies would have a positive effect, based upon an algorithm trained and validated with a validation dataset derived from a subset of the population of subjects. In particular, colorectal cancer in this first variation is a cancerous disease that is typically assessed using one or more of: sigmoidoscopy, colonoscopy, medical imaging (e.g., computed tomography, positron emission tomography, magnetic resonance imaging, etc.), and immunochemistry assays. In the first variation, a set of features useful for diagnostics associated with colorectal cancer includes features derived from one or more of the following taxa: Bacillaceae (family), *Streptococcus pseudopneumoniae* (species), and *Bacteroides fragilis* (species).

Additionally or alternatively, the set of features associated with colorectal cancer can be derived from one or more of: COG derived features, KEGG L2, L3, L4 derived features, and any other suitable functional features. Thus, characterization of the subject comprises characterization of the subject as someone with colorectal cancer based upon detection of one or more of the above features, in a manner that is an alternative or supplemental to typical methods of diagnosis. In variations of the specific example, the set of features can, however, include any other suitable features useful for diagnostics.

1.4.4 Multiple Sclerosis Characterization

In another implementation, a characterization process of Block S140 based upon statistical analyses can identify the sets of features that have the highest correlations with Multiple sclerosis, for which one or more therapies would have a positive effect, based upon an algorithm trained and validated with a validation dataset derived from a subset of the population of subjects. In particular, Multiple sclerosis in this first variation is an inflammatory disease characterized by damage to nervous system cells and tissue, as typically assessed by medical imaging and/or testing of cerebrospinal fluid for evidence of chronic inflammation. In the first variation, a set of features useful for diagnostics associated with Multiple sclerosis includes features derived from one or more of the following taxa: *Lactococcus* (genus).

Additionally or alternatively, the set of features associated with Multiple sclerosis can be derived from one or more of the following taxa: Verrucomicrobiae (class), Verrucomicrobiales (order), *Anaerostipes* (genus), Lachnospiraceae (family), Cyanobacteria (phylum), *Peptococcus* (genus), *Coprococcus comes* (species), *Clostridiales* bacterium A2-162 (species), Prevotellaceae (family), *Prevotella* (genus), butyrate-producing bacterium L1-93 (species), *Actinobacillus porcinus* (species), *Actinobacillus* (genus), Pasteurellaceae (family), Pasteurellales (order), and Actinomycetales (order).

Additionally or alternatively, the set of features associated with multiple sclerosis can be derived from one or more of: COG derived features, KEGG L2, L3, L4 derived features, and any other suitable functional features. Thus, characterization of the subject comprises characterization of the subject as someone with Multiple sclerosis based upon detection of one or more of the above features, in a manner that is an alternative or supplemental to typical methods of diagnosis. In variations of the specific example, the set of features can, however, include any other suitable features useful for diagnostics.

1.4.5 Parkinson's Disease Characterization

In another implementation, a characterization process of Block S140 based upon statistical analyses can identify the sets of features that have the highest correlations with Parkinson's disease, for which one or more therapies would have a positive effect, based upon an algorithm trained and validated with a validation dataset derived from a subset of the population of subjects. In particular, Parkinson's disease in this first variation is a degenerative disorder of the nervous system typically characterized by assessment of medical history and a neurological examination. In the first variation, a set of features useful for diagnostics associated with Parkinson's disease includes features derived from one or more of the following taxa: *Subdoligranulum* sp. 4354A2FAA (species), *Faecalibacterium* (genus), *Faecalibacterium prausnitzii* (species), Enterobacteriales (order), Enterobacteriaceae (family), Cyanobacteria (phylum), *Anaerostipes* (genus), environmental samples (no rank), Peptostreptococcaceae (family), *Anaerostipes hadrus* (species), Bifidobacteriaceae (family), Bifidobacteriales (order), Lactobacillaceae (family), *Lactobacillus* (genus), Christensenellaceae (family), unclassified Peptostreptococcaceae (no rank), Peptostreptococcaceae bacterium TM5 (species), unclassified Peptostreptococcaceae (family), and Tenericutes (phylum).

Additionally or alternatively, the set of features associated with Parkinson's disease can be derived from one or more of: COG derived features, KEGG L2, L3, L4 derived features, and any other suitable functional features. Thus, characterization of the subject comprises characterization of the subject as someone with Parkinson's disease based upon detection of one or more of the above features, in a manner that is an alternative or supplemental to typical methods of diagnosis. In variations of the specific example, the set of features can, however, include any other suitable features useful for diagnostics.

1.4.6 Sjogren's Syndrome Characterization

In another implementation, a characterization process of Block S140 based upon statistical analyses can identify the sets of features that have the highest correlations with Sjogren's Syndrome for which one or more therapies would have a positive effect, based upon an algorithm trained and validated with a validation dataset derived from a subset of the population of subjects. In particular, Sjogren's Syndrome in this first variation is a chronic autoimmune disease characterized by destruction of exocrine glands, as typically assessed using blood tests (e.g., for rheumatoid factor, for antinuclear antibody), the rose bengal test, Schirmer's test, and radiological assessment. In the first variation, a set of features useful for diagnostics associated with Sjogren's Syndrome includes features derived from one or more of the following taxa: Oceanospirillales (order), *Adlercreutzia* (genus), and *Adlercreutzia equolifaciens* (species).

Additionally or alternatively, the set of features associated with Sjogren's Syndrome can be derived from one or more of: COG derived features, KEGG L2, L3, L4 derived features, and any other suitable functional features. Thus, characterization of the subject comprises characterization of the subject as someone with Sjogren's Syndrome based upon detection of one or more of the above features, in a manner that is an alternative or supplemental to typical methods of diagnosis. In variations of the specific example, the set of features can, however, include any other suitable features useful for diagnostics.

1.4.7 Stroke Characterization

In another implementation, a characterization process of Block S140 based upon statistical analyses can identify the sets of features that have the highest correlations with stroke for which one or more therapies would have a positive effect, based upon an algorithm trained and validated with a validation dataset derived from a subset of the population of subjects. In particular, stroke in this first variation is a complication of a cardiovascular disorder characterized by poor blood flow to the brain, as typically assessed by neurological examination, computed tomography, magnetic resonance imaging, Doppler ultrasound, and/or arteriography. In the first variation, a set of features useful for diagnostics associated with stroke includes features derived from one or more of the following taxa: *Cronobacter* (genus), *Cronobacter sakazakii* (species), Gammaproteobacteria (class), *Clostridiales* bacterium A2-162 (species), *Barnesiella* (genus), Erysipelotrichaceae (family), and Pseudomonadales (order).

Additionally or alternatively, the set of features associated with stroke can be derived from one or more of: COG derived features, KEGG L2, L3, L4 derived features, and any other suitable functional features. Thus, characterization of the subject comprises characterization of the subject as someone with stroke based upon detection of one or more of the above features, in a manner that is an alternative or supplemental to typical methods of diagnosis. In variations of the specific example, the set of features can, however, include any other suitable features useful for diagnostics.

Characterization of the subject(s) can additionally or alternatively implement use of a high false positive test and/or a high false negative test to further analyze sensitivity of the characterization process in supporting analyses generated according to embodiments of the method 100.

Furthermore, in relation to the method(s) described above, a deep sequencing approach can allow for determination of a sufficient number of copies of DNA sequences to determine relative amount of corresponding bacteria or genetic pathways in the sample. Having identified one or more of the features described in Sections 1.4.1-1.4.7 above, one can now diagnose autoimmune conditions in individuals by detecting one or more of the above features by any quantitative detection method. For example, while deep sequencing can be used to detect the presence, absence or amount of one or more option in Sections 1.4.1-1.4.7, one can also use other detection methods. For example, without intending to limit the scope of the invention, one could use protein-based diagnostics such as immunoassays to detect bacterial taxa by detecting taxon-specific protein markers.

1.5 First Method: Therapy Models and Provision

As shown in FIG. 1A, in some variations, the first method 100 can further include Block S150, which recites: based upon the characterization model, generating a therapy model configured to correct or otherwise improve a state of the mental health associated condition. Block S150 functions to identify or predict therapies (e.g., probiotic-based therapies, prebiotic-based therapies, phage-based therapies, small molecule-based therapies, etc.) that can shift a subject's microbiome composition and/or functional features toward a desired equilibrium state in promotion of the subject's health. In Block S150, the therapies can be selected from therapies including one or more of: probiotic therapies, phage-based therapies, prebiotic therapies, small molecule-based therapies, cognitive/behavioral therapies, physical rehabilitation therapies, clinical therapies, medication-based therapies, diet-related therapies, and/or any other suitable therapy designed to operate in any other suitable manner in promoting a user's health. In a specific example of a bacteriophage-based therapy, one or more populations (e.g., in terms of colony forming units) of bacteriophages specific to a certain bacteria (or other microorganism) represented in a subject with the mental health associated condition can be used to down-regulate or otherwise eliminate populations of the certain bacteria. As such, bacteriophage-based therapies can be used to reduce the size(s) of the undesired population(s) of bacteria represented in the subject. Complementarily, bacteriophage-based therapies can be used to increase the relative abundances of bacterial populations not targeted by the bacteriophage(s) used.

For instance, in relation to the variations of mental health associated conditions in Sections 1.4.1 through 1.4.7 above, therapies (e.g., probiotic therapies, bacteriophage-based therapies, prebiotic therapies, etc.) can be configured to downregulate and/or upregulate microorganism populations or subpopulations (and/or functions thereof) associated with features characteristic of the mental health associated condition.

In one such variation, the Block S150 can include one or more of the following steps: obtaining a sample from the subject; purifying nucleic acids (e.g., DNA) from the sample; deep sequencing nucleic acids from the sample so as to determine the amount of one or more of the features of one or more of Sections 1.4.1-1.4.7; and comparing the resulting amount of each feature to one or more reference amounts of the one or more of the features listed in one or more of Sections 1.4.1-1.4.7 as occurs in an average individual having a mental health associated condition or an individual not having the mental health associated condition or both. The compilation of features can sometimes be referred to as a "disease signature" for a specific disease. The disease signature can act as a characterization model, and may include probability distributions for control population (no disease) or condition populations having the disease or both. The disease signature can include one or more of the features (e.g., bacterial taxa or genetic pathways) in the sections and can optionally include criteria determined from abundance values of the control and/or condition populations. Example criteria can include cutoff or probability values for amounts of those features associated with average healthy or diseased individuals.

Figure 5:
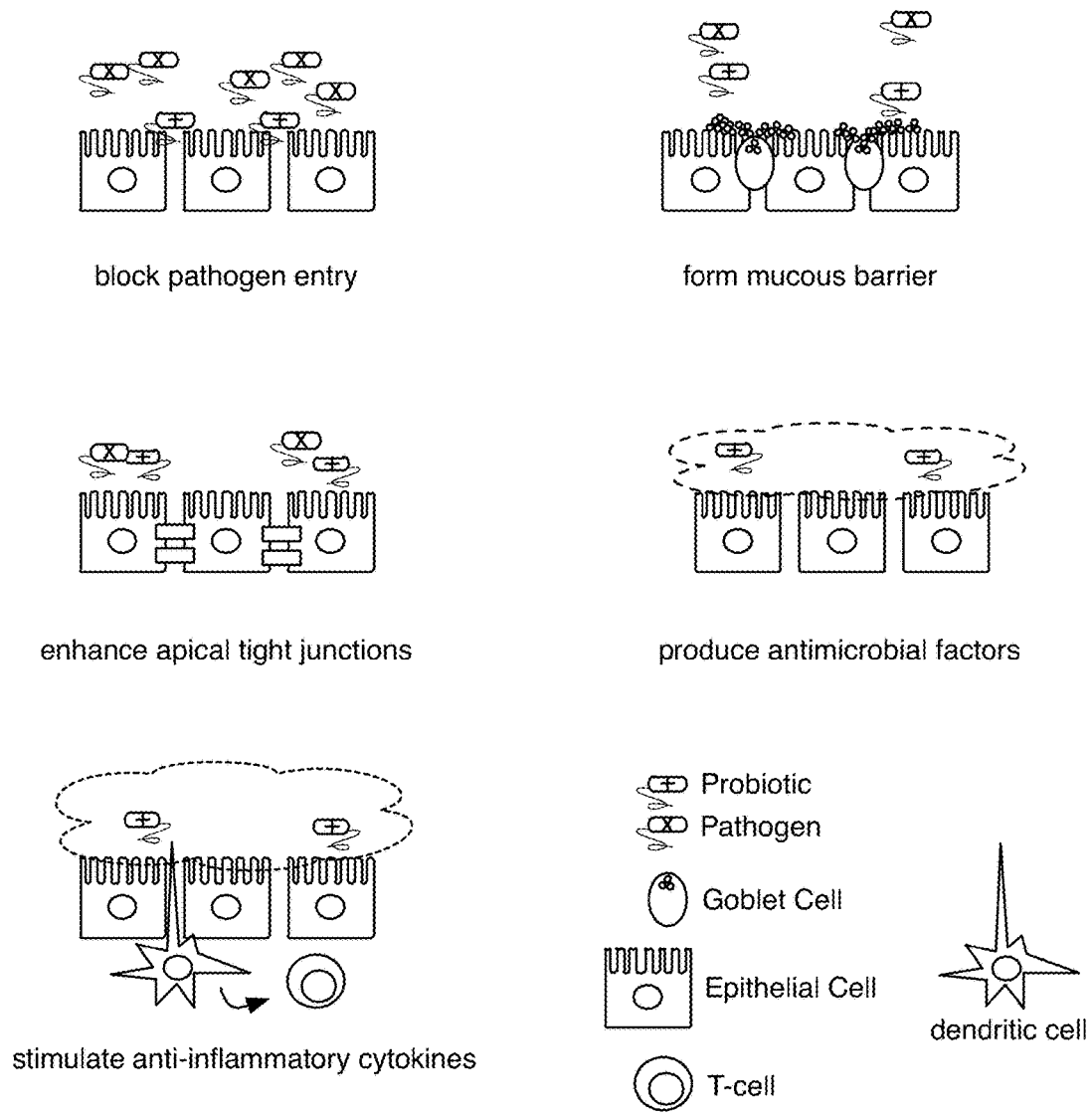
FIG. 5 depicts variations of mechanisms by which probiotic-based therapies operate in an embodiment of a method for characterizing a health condition.

In a specific example of probiotic therapies, as shown in FIG. 5, candidate therapies of the therapy model can perform one or more of: blocking pathogen entry into an epithelial cell by providing a physical barrier (e.g., by way of colonization resistance), inducing formation of a mucous barrier by stimulation of goblet cells, enhance integrity of apical tight junctions between epithelial cells of a subject (e.g., by stimulating up regulation of zona-occludens 1, by preventing tight junction protein redistribution), producing antimicrobial factors, stimulating production of anti-inflammatory cytokines (e.g., by signaling of dendritic cells and induction of regulatory T-cells), triggering an immune response, and performing any other suitable function that adjusts a subject's microbiome away from a state of dysbiosis.

In variations, the therapy model is preferably based upon data from a large population of subjects, which can comprise the population of subjects from which the microbiome-related datasets are derived in Block S110, wherein microbiome composition and/or functional features or states of health, prior exposure to and post exposure to a variety of therapeutic measures, are well characterized. Such data can be used to train and validate the therapy provision model, in identifying therapeutic measures that provide desired outcomes for subjects based upon different microbiome characterizations. In variations, support vector machines, as a supervised machine learning algorithm, can be used to generate the therapy provision model. However, any other suitable machine learning algorithm described above can facilitate generation of the therapy provision model.

While some methods of statistical analyses and machine learning are described in relation to performance of the Blocks above, variations of the method 100 can additionally or alternatively utilize any other suitable algorithms in performing the characterization process. In variations, the algorithm(s) can be characterized by a learning style including any one or more of: supervised learning (e.g., using logistic regression, using back propagation neural networks), unsupervised learning (e.g., using an Apriori algorithm, using K-means clustering), semi-supervised learning, reinforcement learning (e.g., using a Q-learning algorithm, using temporal difference learning), and any other suitable learning style. Furthermore, the algorithm(s) can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked autoencoder method, etc.), a dimensionality reduction method (e.g., principal component analysis, partial lest squares regression, Sammon mapping, multidimensional scaling, projection pursuit, etc.), an ensemble method (e.g., boosting, bootstrapped aggregation, AdaBoost, stacked generalization, gradient boosting machine method, random forest method, etc.), and any suitable form of algorithm.

Additionally or alternatively, the therapy model can be derived in relation to identification of a "normal" or baseline microbiome composition and/or functional features, as assessed from subjects of a population of subjects who are identified to be in good health. Upon identification of a subset of subjects of the population of subjects who are characterized to be in good health (e.g., using features of the characterization process), therapies that modulate microbiome compositions and/or functional features toward those of subjects in good health can be generated in Block S150. Block S150 can thus include identification of one or more baseline microbiome compositions and/or functional features (e.g., one baseline microbiome for each of a set of demographics), and potential therapy formulations and therapy regimens that can shift microbiomes of subjects who are in a state of dysbiosis toward one of the identified baseline microbiome compositions and/or functional features. The therapy model can, however, be generated and/or refined in any other suitable manner.

Microorganism compositions associated with probiotic therapies associated with the therapy model preferably include microorganisms that are culturable (e.g., able to be expanded to provide a scalable therapy) and non-lethal (e.g., non-lethal in their desired therapeutic dosages). Furthermore, microorganism compositions can comprise a single type of microorganism that has an acute or moderated effect upon a subject's microbiome. Additionally or alternatively, microorganism compositions can comprise balanced combinations of multiple types of microorganisms that are configured to cooperate with each other in driving a subject's microbiome toward a desired state. For instance, a combination of multiple types of bacteria in a probiotic therapy can comprise a first bacteria type that generates products that are used by a second bacteria type that has a strong effect in positively affecting a subject's microbiome. Additionally or alternatively, a combination of multiple types of bacteria in a probiotic therapy can comprise several bacteria types that produce proteins with the same functions that positively affect a subject's microbiome.

In examples of probiotic therapies, probiotic compositions can comprise components of one or more of the identified taxa of microorganisms (e.g., as described in sections 1.4.1 through 1.4.7 above) provided at dosages of 1 million to 10 billion CFUs, as determined from a therapy model that predicts positive adjustment of a subject's microbiome in response to the therapy. Additionally or alternatively, the therapy can comprise dosages of proteins resulting from functional presence in the microbiome compositions of subjects without the mental health associated condition. In the examples, a subject can be instructed to ingest capsules comprising the probiotic formulation according to a regimen tailored to one or more of his/her: physiology (e.g., body mass index, weight, height), demographics (e.g., gender, age), severity of dysbiosis, sensitivity to medications, and any other suitable factor.

Furthermore, probiotic compositions of probiotic-based therapies can be naturally or synthetically derived. For instance, in one application, a probiotic composition can be naturally derived from fecal matter or other biological matter (e.g., of one or more subjects having a baseline microbiome composition and/or functional features, as identified using the characterization process and the therapy model). Additionally or alternatively, probiotic compositions can be synthetically derived (e.g., derived using a benchtop method) based upon a baseline microbiome composition and/or functional features, as identified using the characterization process and the therapy model. In variations, microorganism agents that can be used in probiotic therapies can include one or more of: yeast (e.g., *Saccharomyces boulardii*), gram-negative bacteria (e.g., *E. coli Nissle, Akkermansia muciniphila, Prevotella bryantii*, etc.), gram-positive bacteria (e.g., *Bifidobacterium animalis* (including subspecies *lactis*), *Bifidobacterium longum* (including subspecies *infantis*), *Bifidobacterium bifidum, Bifidobacterium pseudolongum, Bifidobacterium thermophilum, Bifidobacterium breve, Lactobacillus rhamnosus, Lactobacillus acidophilus, Lactobacillus casei, Lactobacillus helveticus, Lactobacillus plantarum, Lactobacillus fermentum, Lactobacillus salivarius, Lactobacillus delbrueckii* (including subspecies *bulgaricus*), *Lactobacillus johnsonii, Lactobacillus reuteri, Lactobacillus gasseri, Lactobacillus brevis* (including subspecies *coagulans*), *Bacillus cereus, Bacillus subtilis* (including var. *Natto*), *Bacillus polyfermenticus, Bacillus dausii, Bacillus licheniformis, Bacillus coagulans, Bacillus pumilus, Faecalibacterium prausnitzii, Streptococcus thermophiles, Brevibacillus brevis, Lactococcus lactis, Leuconostoc mesenteroides, Enterococcus faecium, Enterococcus faecalis, Enterococcus durans, Clostridium butyricum, Sporolactobacillus inulinus, Sporolactobacillus vineae, Pediococcus acidilactic, Pediococcus pentosaceus*, etc.), and any other suitable type of microorganism agent.

Additionally or alternatively, therapies promoted by the therapy model of Block S150 can include one or more of: consumables (e.g., food items, beverage items, nutritional supplements), suggested activities (e.g., exercise regimens, adjustments to alcohol consumption, adjustments to cigarette usage, adjustments to drug usage), topical therapies (e.g., lotions, ointments, antiseptics, etc.), adjustments to hygienic product usage (e.g., use of shampoo products, use of conditioner products, use of soaps, use of makeup products, etc.), adjustments to diet (e.g., sugar consumption, fat consumption, salt consumption, acid consumption, etc.), adjustments to sleep behavior, living arrangement adjustments (e.g., adjustments to living with pets, adjustments to living with plants in one's home environment, adjustments to light and temperature in one's home environment, etc.), nutritional supplements (e.g., vitamins, minerals, fiber, fatty acids, amino acids, prebiotics, probiotics, etc.), medications, antibiotics, and any other suitable therapeutic measure. Among the prebiotics suitable for treatment, as either part of any food or as supplement, are included the following components: 1,4-dihydroxy-2-naphthoic acid (DHNA), Inulin, trans-Galactooligosaccharides (GOS), Lactulose, Mannan oligosaccharides (MOS), Fructooligosaccharides (FOS), Neoagaro-oligosaccharides (NAOS), Pyrodextrins, Xylo-oligosaccharides (XOS), Isomalto-oligosaccharides (IMOS), Amylose-resistant starch, Soybean oligosaccharide (SBOS), Lactitol, Lactosucrose (LS), Isomaltulose (including Palatinose), Arabinoxylooligosaccharides (AXOS), Raffinose oligosaccharides (RFO), Arabinoxylans (AX), Polyphenols or any another compound capable of changing the microbiota composition with a desirable effect.

Additionally or alternatively, therapies promoted by the therapy model of Block S150 can include one or more of: physiological symptom treating therapies (e.g., medications); pain mitigating therapies; sleep improving therapies; relaxation therapies; neural plasticity improving therapies (e.g., transcranial stimulation therapies); different forms of psychological therapies having different therapy orientations (e.g., motivational, psychoeducational, cognitive behavioral, biological, physical, mindfulness-related, relaxation-related, dialectical behavioral, acceptance-related, commitment-related, etc.) configured to address a variety of factors contributing to adverse cognitive states; psychiatric management measures (e.g., education of the patient, education of acquaintances of the patient, forming alliances, providing support groups, etc.); pharmacotherapeutic measures (e.g., antipsychotic medications, benzodiazepines, antidepressants, mood stabilizers, beta blockers); psychotherapeutic measures (e.g., cognitive behavioral therapy, interpersonal therapy, problem solving therapy, psychodynamic psychotherapy); psychosocial interventions; weight management interventions (e.g., to prevent adverse weight-related side effects due to medications); electroconvulsive therapeutic measures; physical therapy rehabilitation measures; and any other suitable type of therapy for improving the mental health associated condition.

The first method 100 can, however, include any other suitable blocks or steps configured to facilitate reception of biological samples from individuals, processing of biological samples from individuals, analyzing data derived from biological samples, and generating models that can be used to provide customized diagnostics and/or therapeutics according to specific microbiome compositions of individuals.

1.6 Example Method

Embodiments can provide a method for determining a classification of the presence or absence for a condition and/or determine a course of treatment for an individual human having the condition. The method can be performed by a computer system.

In step 1, sequence reads of bacterial DNA obtained from analyzing a test sample from the individual human are received. The analysis can be done with various techniques, e.g., as described herein, such as sequencing or hybridization arrays. The sequence reads can be received at a computer system, e.g., from a detection apparatus, such as a sequencing machine that provides data to a storage device (which can be loaded into the computer system) or across a network to the computer system.

In step 2, the sequence reads are mapped to a bacterial sequence database to obtain a plurality of mapped sequence reads. The bacterial sequence database includes a plurality of reference sequences of a plurality of bacteria. The reference sequences can be for predetermined region(s) of the bacteria, e.g., the 16S region.

In step 3, the mapped sequence reads are assigned to sequence groups based on the mapping to obtain assigned sequence reads assigned to at least one sequence group. A sequence group includes one or more of the plurality of reference sequences. The mapping can involve the sequence reads being mapped to one or more predetermined regions of the reference sequences. For example, the sequence reads can be mapped to the 16S gene. Thus, the sequence reads do not have to be mapped to the whole genome, but only to the region(s) covered by the reference sequences of a sequence group.

In step 4, a total number of assigned sequence reads is determined. In some embodiments, the total number of assigned reads can include reads identified as being bacterial, but not assigned to a known sequence group. In other embodiments, the total number can be a sum of sequence reads assigned to known sequence groups, where the sum may include any sequence read assigned to at least one sequence group.

In step 5, relative abundance value(s) can be determined. For example, for each sequence group of a disease signature set of one or more sequence groups associated with features described in Sections 1.4.1-1.4.7 above, a relative abundance value of assigned sequence reads assigned to the sequence group relative to the total number of assigned sequence reads can be determined. The relative abundance values can form a test feature vector, where each value of the test feature vector is an RAV of a different sequence group.

In step 6, the test feature vector is compared to calibration feature vectors generated from relative abundance values of calibration samples having a known status of the condition. The calibration samples may be samples of a condition population and samples of a control population. In some embodiments, the comparison can involve various machine learning techniques, such as supervised machine learning (e.g. decision trees, nearest neighbor, support vector machines, neural networks, naïve Bayes classifier, etc.) and unsupervised machine learning (e.g., clustering, principal component analysis, etc.).

In one embodiment, clustering can use a network approach, where the distance between each pair of samples in the network is computed based on the relative abundance of the sequence groups that are relevant for each condition. Then, a new sample can be compared to all samples in the network, using the same metric based on relative abundance, and it can be decided to which cluster it should belong. A meaningful distance metric would allow all diseased individuals to form one or a few clusters and all healthy individuals to form one or a few clusters. One distance metric is the Bray-Curtis dissimilarity, or equivalently a similarity network, where the metric is 1−Bray-Curtis dissimilarity. Another example distance metric is the Tanimoto coefficient.

In some embodiments, the feature vectors may be compared by transforming the RAVs into probability values, thereby forming probability vectors. Similar processing for the feature vectors can be performed for the probability, with such a process still involving a comparison of the feature vectors since the probability vectors are generated from the feature vectors.

Step 7 can determine a classification of the presence or absence of the mental health associated condition and/or determine a course of treatment for an individual human having mental health associated condition based on the comparing. For example, the cluster to which the test feature vector is assigned may be a condition cluster, and the classification can be made that the individual human has the condition or a certain probability for having the condition.

In one embodiment involving clustering, the calibration feature vectors can be clustered into a control duster not having the condition and a condition duster having the condition. Then, which cluster the test feature vector belongs can be determined. The identified duster can be used to determine the classification or select a course of treatment. In one implementation, the clustering can use a Bray-Curtis dissimilarity.

In one embodiment involving a decision tree, the comparison may be performed to by comparing the test feature vector to one or more cutoff values (e.g., as a corresponding cutoff vector), where the one or more cutoff values are determined from the calibration feature vectors, thereby providing the comparison. Thus, the comparing can include comparing each of the relative abundance values of the test feature vector to a respective cutoff value determined from the calibration feature vectors generated from the calibration samples. The respective cutoff values can be determined to provide an optimal discrimination for each sequence group.

A new sample can be measured to detect the RAVs for the sequence groups in the disease signature. The RAV for each sequence group can be compared to the probability distributions for the control and conditions populations for the particular sequence group. For example, the probability distribution for the condition population can provide an output of a probability (condition probability) of having the condition for a given input of the RAV. Similarly, the probability distribution for the control population can provide an output of a probability (control probability) of not having the condition for a given input of the RAV. Thus, the value of the probability distribution at the RAV can provide the probability of the sample being in each of the populations. Thus, it can be determined which population the sample is more likely to belong to, by taking the maximum probability.

A total probability across sequence groups of a disease signature can be used. For all of the sequence groups that are measured, a condition probability can be determined for whether the sample is in the condition group and a control probability can be determined for whether the sample is in the control population. In other embodiments, just the condition probabilities or just the control probabilities can be determined.

The probabilities across the sequence groups can be used to determine a total probability. For example, an average of the condition probabilities can be determined, thereby obtaining a final condition probability of the subject having the condition based on the disease signature. An average of the control probabilities can be determined, thereby obtaining a final control probability of the subject not having the condition based on the disease signature.

In one embodiment, the final condition probability and final control probability can be compared to each other to determine the final classification. For instance, a difference between the two final probabilities can be determined, and a final classification probability determined from the difference. A large positive difference with final condition probability being higher would result in a higher final classification probability of the subject having the disease.

In other embodiments, only the final condition probability can be used to determine the final classification probability. For example, the final classification probability can be the final condition probability. Alternatively, the final classification probability can be one minus the final control probability, or 100% minus the final control probability depending on the formatting of the probabilities.

In some embodiments, a final classification probability for one disease of a class can be combined with other final classification probabilities of other diseases of the same class. The aggregated probability can then be used to determine whether the subject has at least one of the classes of diseases. Thus, embodiments can determine whether a subject has a health issue that may include a plurality of diseases associated with that health issue.

The classification can be one of the final probabilities. In other examples, embodiments can compare a final probability to a threshold value to make a determination of whether the condition exists. For example, the respective condition probabilities can be averaged, and an average can be compared to a threshold value to determine whether the condition exists. As another example, the comparison of the average to the threshold value can provide a treatment for treating the subject.

2. Method for Generating Microbiome-Derived Diagnostics

In some embodiments, as noted above, outputs of the first method 100 can be used to generate diagnostics and/or provide therapeutic measures for an individual based upon an analysis of the individual's microbiome. As such, a second method 200 derived from at least one output of the first method 100 can include: receiving a biological sample from a subject S210; characterizing the subject with a form of a mental health associated condition based upon processing a microbiome dataset derived from the biological sample S220; and promoting a therapy to the subject with the mental health associated condition based upon the characterization and the therapy model S230.

Block S210 recites: receiving a biological sample from the subject, which functions to facilitate generation of a microbiome composition dataset and/or a microbiome functional diversity dataset for the subject. As such, processing and analyzing the biological sample preferably facilitates generation of a microbiome composition dataset and/or a microbiome functional diversity dataset for the subject, which can be used to provide inputs that can be used to characterize the individual in relation to diagnosis of the mental health associated condition, as in Block S220. Receiving a biological sample from the subject is preferably performed in a manner similar to that of one of the embodiments, variations, and/or examples of sample reception described in relation to Block S110 above. As such, reception and processing of the biological sample in Block S210 can be performed for the subject using similar processes as those for receiving and processing biological samples used to generate the characterization(s) and/or the therapy provision model of the first method 100, in order to provide consistency of process. However, biological sample reception and processing in Block S210 can alternatively be performed in any other suitable manner.

Block S220 recites: characterizing the subject characterizing the subject with a form of mental health associated condition based upon processing a microbiome dataset derived from the biological sample. Block S220 functions to extract features from microbiome-derived data of the subject, and use the features to positively or negatively characterize the individual as having a form of the mental health associated condition. Characterizing the subject in Block S220 thus preferably includes identifying features and/or combinations of features associated with the microbiome composition and/or functional features of the microbiome of the subject, and comparing such features with features characteristic of subjects with the mental health associated condition. Block S220 can further include generation of and/or output of a confidence metric associated with the characterization for the individual. For instance, a confidence metric can be derived from the number of features used to generate the classification, relative weights or rankings of features used to generate the characterization, measures of bias in the models used in Block S140 above, and/or any other suitable parameter associated with aspects of the characterization operation of Block S140.

In some variations, features extracted from the microbiome dataset can be supplemented with survey-derived and/or medical history-derived features from the individual, which can be used to further refine the characterization operation(s) of Block S220. However, the microbiome composition dataset and/or the microbiome functional diversity dataset of the individual can additionally or alternatively be used in any other suitable manner to enhance the first method 100 and/or the second method 200.

Block S230 recites: promoting a therapy to the subject with the mental health associated condition based upon the characterization and the therapy model. Block S230 functions to recommend or provide a personalized therapeutic measure to the subject, in order to shift the microbiome composition of the individual toward a desired equilibrium state. As such, Block S230 can include correcting the mental health associated condition, or otherwise positively affecting the user's health in relation to the mental health associated condition. Block S230 can thus include promoting one or more therapeutic measures to the subject based upon their characterization in relation to the mental health associated condition, as described in relation to Sections 1.4.1 through 1.4.7 above, wherein the therapy is configured to modulate taxonomic makeup of the subject's microbiome and/or modulate functional feature aspects of the subject in a desired manner toward a "normal" state in relation to the characterizations described above.

In Block S230, providing the therapeutic measure to the subject can include recommendation of available therapeutic measures configured to modulate microbiome composition of the subject toward a desired state. Additionally or alternatively, Block S230 can include provision of customized therapy to the subject according to their characterization (e.g., in relation to a specific type of mental health associated condition). In variations, therapeutic measures for adjusting a microbiome composition of the subject, in order to improve a state of the mental health associated condition can include one or more of: probiotics, prebiotics, bacteriophage-based therapies, consumables, suggested activities, topical therapies, adjustments to hygienic product usage, adjustments to diet, adjustments to sleep behavior, living arrangement, adjustments to level of sexual activity, nutritional supplements, medications, antibiotics, and any other suitable therapeutic measure. Therapy provision in Block S230 can include provision of notifications by way of an electronic device, through an entity associated with the individual, and/or in any other suitable manner.

Figure 6:
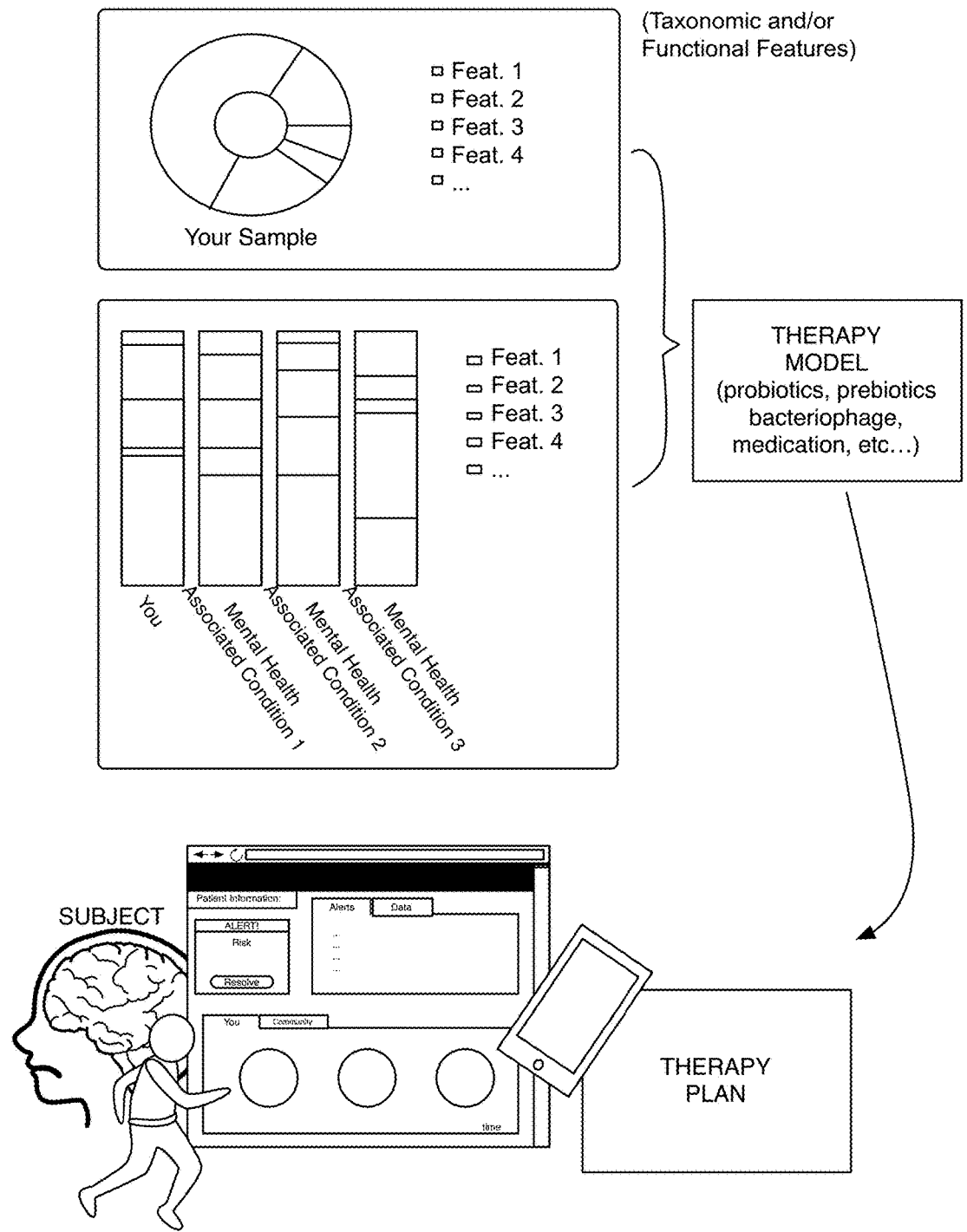
FIG. 6 depicts examples of therapy-related notification provision in an example of a method for generating microbiome-derived diagnostics and therapeutics.

In more detail, therapy provision in Block S230 can include provision of notifications to the subject regarding recommended therapeutic measures and/or other courses of action, in relation to health-related goals, as shown in FIG. 6. Notifications can be provided to an individual by way of an electronic device (e.g., personal computer, mobile device, tablet, head-mounted wearable computing device, wrist-mounted wearable computing device, etc.) that executes an application, web interface, and/or messaging client configured for notification provision. In one example, a web interface of a personal computer or laptop associated with a subject can provide access, by the subject, to a user account of the subject, wherein the user account includes information regarding the subject's characterization, detailed characterization of aspects of the subject's microbiome composition and/or functional features, and notifications regarding suggested therapeutic measures generated in Block S150. In another example, an application executing at a personal electronic device (e.g., smart phone, smart watch, head-mounted smart device) can be configured to provide notifications (e.g., at a display, haptically, in an auditory manner, etc.) regarding therapeutic suggestions generated by the therapy model of Block S150. Notifications can additionally or alternatively be provided directly through an entity associated with a subject (e.g., a caretaker, a spouse, a significant other, a healthcare professional, etc.). In some further variations, notifications can additionally or alternatively be provided to an entity (e.g., healthcare professional) associated with the subject, wherein the entity is able to administer the therapeutic measure (e.g., by way of prescription, by way of conducting a therapeutic session, etc.). Notifications can, however, be provided for therapy administration to the subject in any other suitable manner.

Furthermore, in an extension of Block S230, monitoring of the subject during the course of a therapeutic regimen (e.g., by receiving and analyzing biological samples from the subject throughout therapy, by receiving survey-derived data from the subject throughout therapy) can be used to generate a therapy-effectiveness model for each recommended therapeutic measure provided according to the model generated in Block S150.

The methods 100, 200 and/or system of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a patient computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the embodiments of the invention without departing from the scope of this invention as defined in the following claims.

We claim:

1. A method for at least one of characterizing, diagnosing, and treating a mental health associated condition for a subject, the method comprising:
    for each sample of a set of samples comprising at least one sample associated with the mental health associated condition:
        determining a microorganism nucleic acid sequence, comprising:
            selecting a primer for a nucleic acid sequence,
            amplifying nucleic acid material from the sample using the selected primer; and
            determining an alignment of the microorganism nucleic acid sequence to a reference nucleic acid sequence;
    generating at least one of a microbiome composition diversity dataset and a microbiome functional diversity dataset based on the alignments;
    generating a characterization of the mental health associated condition based on the at least one of the microbiome composition diversity dataset and the microbiome functional diversity dataset;
    determining a therapy for the subject based on the characterization and a subject sample from the subject; and
    providing the therapy to the subject, wherein the therapy is operable to modulate microbiome composition to improve a state of the mental health associated condition.

2. The method of claim 1, further comprising:
    providing a set of sampling kits to a set of subjects associated with the set of samples, each sampling kit of the set of sampling kits comprising a sample container configured to receive the sample from a collection site,
    wherein determining the microorganism nucleic acid sequence comprises determining the microorganism nucleic acid sequence with a bridge amplification substrate of a next generation sequencing platform of a sample processing system, and
    wherein generating the at least one of the microbiome composition diversity dataset and the microbiome functional diversity dataset comprises generating the at least one of the microbiome composition diversity dataset and the microbiome functional diversity dataset at computing devices operable to communicate with the next generation sequencing platform.

3. The method of claim 2, wherein the nucleic acid material comprises fragmented nucleic acid material, and wherein determining the microorganism nucleic acid sequence comprises performing, at a library preparation subsystem of the sample processing system, multiplex amplification with the fragmented nucleic acid material based on the selected primer.

4. The method of claim 1, wherein generating the characterization comprises analyzing a set of features extracted from the at least one of the microbiome composition diversity dataset and the microbiome functional diversity dataset, wherein the set of features is associated with at least one of: presence of a microbiome feature from the set of features, absence of the microbiome feature from the set of features, relative abundance of different taxonomic groups represented in the microbiome composition diversity dataset, a ratio between at least two features associated with the different taxonomic groups and functional features, interactions between the different taxonomic groups represented in the microbiome composition diversity dataset, and phylogenetic distance between the different taxonomic groups represented in the microbiome composition diversity dataset.

5. The method of claim 4, wherein generating the characterization comprises analyzing the set of features extracted from the at least one of the microbiome composition diversity dataset and the microbiome functional diversity dataset with a statistical analysis comprising at least one of: a prediction analysis, multi hypothesis testing, a random forest test, and principal component analysis.

6. The method of claim 1, wherein generating the characterization of the mental health associated condition comprises generating the characterization associated with diagnosis of at least one of: an acid reflux condition, an AIDS condition, and a colorectal cancer condition.

7. The method of claim 6, wherein generating the characterization associated with the diagnosis comprises generating the characterization based on a set of microbiome composition features extracted from the microbiome composition diversity dataset, and wherein the set of microbiome composition features is associated with a set of taxa comprising at least one of: *Sarcina* (genus), *Blautia* (genus), *Terrisporobacter* (genus), *Faecalibacterium* (genus), *Moryella* (genus), *Lactobacillus* (genus), *Clostridium* (genus), *Odoribacter* (genus), *Thalassospira* (genus), *Barnesiella* (genus), *Subdoligranulum* (genus), *Bifidobacterium* (genus), *Anaerotruncus* (genus), *Streptococcus* (genus), *Parabacteroides* (genus), *Alistipes* (genus), *Erysipelatoclostridium* (genus), *Bacteroides* (genus), *Methanobrevibacter* (genus), *Phascolarctobacterium, Butyricimonas* (genus), Clostridiaceae (family), Lactobacillaceae (family), Ruminococcaceae (family), Rhodospirillaceae (family), Lachnospiraceae (family), Bifidobacteriaceae (family), Flavobacteriaceae (family), Rikenellaceae (family), Sutterellaceae (family), Bacteroidaceae (family), Peptostreptococcaceae (family), Veillonellaceae (family), Oscillospiraceae (family), Methanobacteriaceae (family), Prevotellaceae (family), Rhodospirillales (order), Bifidobacteriales (order), Flavobacteriales (order), Burkholderiales (order), Alphaproteobacteria (class), Flavobacteria (class), Betaproteobacteria (class), Methanobacteria (class), Bacteroidia (class), Proteobacteria (phylum), Euryarchaeota (phylum), Verrucomicrobia (phylum), Bacteroidetes (phylum), *Prevotella* (genus), *Megasphaera* (genus), Erysipelotrichaceae (family), Bacteroidetes/Chlorobi group (superphylum), Bacteroidales (order), Selenomonadales (order), Negativicutes (class), *Coprococcus* (genus), Porphyromonadaceae (family), Acidaminococcaceae (family), *Lachnospira* (genus), *Parasutterella* (genus), *Parasutterella excrementihominis* (species), *Eubacterium ramulus* (species), Bacillaceae (family), *Streptococcus pseudopneumoniae* (species), and *Bacteroides fragilis* (species).

8. The method of claim 7, wherein generating the characterization associated with the diagnosis comprises generating the characterization based on the set of microbiome composition features and a set of microbiome functional diversity features extracted from the microbiome functional diversity dataset, wherein the set of microbiome functional diversity features comprises at least one of: a cell motility Kyoto Encyclopedia of Genes and Genomes (KEGG) L2 derived feature; a carbohydrate metabolism KEGG L2 derived feature; an environmental adaptation KEGG L2 derived feature; a signaling molecules and interaction KEGG L2 derived feature; a metabolism KEGG L2 derived feature; an energy metabolism KEGG L2 derived feature; a signal transduction KEGG L2 derived feature; a xenobiotics biodegradation and metabolism KEGG L2 derived feature; a translation KEGG L2 derived feature; a lipid metabolism KEGG L2 derived feature; a metabolism of other amino acids KEGG L2 derived feature; an immune system diseases KEGG L2 derived feature; a secretion system KEGG L3 derived feature; a selenocompound metabolism KEGG L3 derived feature; a fructose and mannose metabolism KEGG L3 derived feature; a bacterial chemotaxis KEGG L3 derived feature; an amino acid metabolism KEGG L3 derived feature; a plant-pathogen interaction KEGG L3 derived feature; a bacterial toxins KEGG L3 derived feature; a pyruvate metabolism KEGG L3 derived feature; a general function prediction KEGG L3 derived feature; a nitrogen metabolism KEGG L3 derived feature; a two-component system KEGG L3 derived feature; a ribosome biogenesis KEGG L3 derived feature; a propanoate metabolism KEGG L3 derived feature; a tuberculosis KEGG L3 derived feature; a fatty acid biosynthesis KEGG L3 derived feature; a oxidative phosphorylation KEGG L3 derived feature; a Glyoxylate and dicarboxylate metabolism KEGG L3 derived feature; an Alzheimer's disease KEGG L3 derived feature; a biotin metabolism KEGG L3 derived feature; a pentose phosphate pathway KEGG L3 derived feature; a galactose metabolism KEGG L3 derived feature; a methane metabolism KEGG L3 derived feature; a ribosome biogenesis in eukaryotes KEGG L3 derived feature; a bacterial secretion system KEGG L3 derived feature; a beta-Alanine metabolism KEGG L3 derived feature; a pentose and glucuronate interconversions KEGG L3 derived feature; a polyketide sugar unit biosynthesis KEGG L3 derived feature; a streptomycin biosynthesis KEGG L3 derived feature; a protein export KEGG L3 derived feature; an Aminoacyl-tRNA biosynthesis KEGG L3 derived feature; a chloroalkane and chloroalkene degradation KEGG L3 derived feature; a translation proteins KEGG L3 derived feature; a folate biosynthesis KEGG L3 derived feature; a phosphotransferase system KEGG L3 derived feature; an other transporters KEGG L3 derived feature; a glycerophospholipid metabolism KEGG L3 derived feature; a glycine, serine, and threonine metabolism KEGG L3 derived feature; a terpenoid backbone biosynthesis KEGG L3 derived feature; a riboflavin metabolism KEGG L3 derived feature; a vitamin metabolism KEGG L3 derived feature; a ribosome KEGG L3 derived feature; a homologous recombination KEGG L3 derived feature; a chromosome KEGG L3 derived feature; an inositol phosphate metabolism KEGG L3 derived feature; a naphthalene degradation KEGG L3 derived feature; a phosphatidylinositol signaling system KEGG L3 derived feature; a taurine and hypotaurine metabolism KEGG L3 derived feature; a neurodegenerative diseases KEGG L2 derived feature; a transcription KEGG L2 derived feature; a metabolism of cofactors and vitamins KEGG L2 derived feature; an endocrine system KEGG L2 derived feature; a cancers KEGG L2 derived feature; an amino acid metabolism KEGG L2 derived feature; a glycolysis/gluconeogenesis KEGG L3 derived feature; a restriction enzyme KEGG L3 derived feature; a PPAR signaling pathway KEGG L3 derived feature; an aminobenzoate degradation KEGG L3 derived feature; a pathways in cancer KEGG L3 derived feature; a mismatch repair KEGG L3 derived feature; a vitamin B6 metabolism KEGG L3 derived feature; a butirosin and neomycin biosynthesis KEGG L3 derived feature; a pantothenate and CoA biosynthesis KEGG L3 derived feature; a zeatin biosynthesis KEGG L3 derived feature; an energy metabolism KEGG L3 derived feature; a limonene and pinene degradation KEGG L3 derived feature; a valine, leucine, and isoleucine biosynthesis KEGG L3 derived feature; a lipopolysaccharide biosynthesis proteins KEGG L3 derived feature; and a transcription machinery KEGG L3 derived feature.

9. The method of claim 7, further comprising:
determining a modulator of a biomolecule associated with the set of taxa and the mental health associated condition; and
deriving a therapeutic composition for the mental health associated condition based on the modulator,
wherein providing the therapy comprises providing the therapeutic composition to the subject based on the characterization.

10. The method of claim 1, wherein generating the characterization of the mental health associated condition comprises generating the characterization associated with diagnosis of at least one of: a multiple sclerosis characterization, a Parkinson's disease condition, a Sjogren's Syndrome condition, and a stroke condition.

11. The method of claim 10, wherein generating the characterization associated with the diagnosis comprises generating the characterization based on a set of microbiome composition features extracted from the microbiome composition diversity dataset, and wherein the set of microbiome composition features is associated with a set of taxa comprising at least one of: *Lactococcus* (genus), Verrucomicrobiae (class), Verrucomicrobiales (order), *Anaerostipes* (genus), Lachnospiraceae (family), Cyanobacteria (phylum), *Peptococcus* (genus), *Coprococcus comes* (species), *Clostridiales* bacterium A2-162 (species), Prevotellaceae (family), *Prevotella* (genus), butyrate-producing bacterium L1-93 (species), *Actinobacillus porcinus* (species), *Actinobacillus* (genus), Pasteurellaceae (family), Pasteurellales (order), Actinomycetales (order), *Subdoligranulum* sp. 4_3_54A2FAA (species), *Faecalibacterium* (genus), *Faecalibacterium prausnitzii* (species), Enterobacteriales (order), Enterobacteriaceae (family), environmental samples (no rank), Peptostreptococcaceae (family), *Anaerostipes hadrus* (species), Bifidobacteriaceae (family), Bifidobacteriales (order), Lactobacillaceae (family), *Lactobacillus* (genus), Christensenellaceae (family), unclassified Peptostreptococcaceae (no rank), Peptostreptococcaceae bacterium TM5 (species), unclassified Peptostreptococcaceae (family), Tenericutes (phylum), Oceanospirillales (order), *Adlercreutzia* (genus), and *Adlercreutzia equolifaciens* (species), *Cronobacter* (genus), *Cronobacter sakazakii* (species), Gammaproteobacteria (class), *Barnesiella* (genus), Erysipelotrichaceae (family), and Pseudomonadales (order).

12. The method of claim 10, wherein selecting the primer comprises selecting the primer associated with damage to a nervous system.

13. A method for at least one of characterizing, diagnosing, and treating a mental health associated condition for a subject, the method comprising:
receiving a sample from the subject associated with the mental health associated condition;
determining a microorganism sequence based on the sample, comprising:
selecting a primer associated with the mental health associated condition, and
amplifying nucleic acid material from the sample based on the selected primer; and
generating a microbiome feature dataset based on the microorganism sequence;
generating a characterization of the mental health associated condition for the subject based on the microbiome feature dataset and a characterization model associated with a population of subjects; and
providing a therapy to the subject based on the characterization, wherein the therapy is operable to facilitate improvement of a state of the mental health associated condition.

14. The method of claim 13, wherein the nucleic acid material comprises fragmented nucleic acid material, wherein determining the microorganism sequence comprises amplifying the fragmented nucleic acid material based on the selected primer, and wherein generating the microbiome feature dataset comprises determining an alignment of the microorganism sequence to reference sequence associated with the mental health associated condition.

15. The method of claim 13, wherein generating the characterization comprises performing a statistical analysis with at least one of a Kolmogorov-Smirnov test and a t-test to assess relative abundance of features from the microbiome feature dataset.

16. The method of claim 13, further comprising:
determining a set of population sequences for the population of subjects, wherein determining the set of population sequences comprises processing a set of samples from the population based on the selected primer;
collecting a supplementary dataset indicative of diagnosis of the mental health associated condition for the population of subjects; and
generating the characterization model based on the set of population sequences and the supplementary dataset.

17. The method of claim 16, wherein the mental health associated condition comprises at least one of an acid reflux condition, a multiple sclerosis condition, and a colorectal cancer condition, and wherein the supplementary dataset comprises medical imaging data collected at a medical imaging system.

18. The method of claim 13, wherein the mental health associated condition comprises an acid reflux condition, and wherein the microbiome feature dataset comprises a set of microbiome composition features and a set of microbiome functional features,
wherein the set of microbiome composition features is associated with a set of taxa comprising at least one of: *Sarcina* (genus), *Blautia* (genus), *Terrisporobacter* (genus), *Faecalibacterium* (genus), *Moryella* (genus), *Lactobacillus* (genus), *Clostridium* (genus), *Odoribacter* (genus), *Thalassospira* (genus), *Barnesiella* (genus), *Subdoligranulum* (genus), *Bifidobacterium* (genus), *Anaerotruncus* (genus), *Streptococcus* (genus), *Parabacteroides* (genus), *Alistipes* (genus), *Erysipelatoclostridium* (genus), *Bacteroides* (genus), *Methanobrevibacter* (genus), *Phascolarctobacterium, Butyricimonas* (genus), Clostridiaceae (family), Lactobacillaceae (family), Ruminococcaceae (family), Rhodospirillaceae (family), Lachnospiraceae (family), Bifidobacteriaceae (family), Flavobacteriaceae (family), Rikenellaceae (family), Sutterellaceae (family), Bacteroidaceae (family), Peptostreptococcaceae (family), Veillonellaceae (family), Oscillospiraceae (family), Methanobacteriaceae (family), Prevotellaceae (family), Rhodospirillales (order), Bifidobacteriales (order), Flavobacteriales (order), Burkholderiales (order), Alphaproteobacteria (class), Flavobacteria (class), Betaproteobacteria (class), Methanobacteria (class), Bacteroidia (class), Proteobacteria (phylum), Euryarchaeota (phylum), Verrucomicrobia (phylum), and Bacteroidetes (phylum), and
wherein the set of microbiome functional features comprises at least one of: a cell motility KEGG L2 derived feature; a carbohydrate metabolism KEGG L2 derived feature; an environmental adaptation KEGG L2 derived feature; a signaling molecules and interaction KEGG L2 derived feature; a metabolism KEGG L2 derived feature; an energy metabolism KEGG L2 derived feature; a signal transduction KEGG L2 derived feature; a xenobiotics biodegradation and metabolism KEGG L2 derived feature; a translation KEGG L2 derived feature; a lipid metabolism KEGG L2 derived feature; a metabolism of other amino acids KEGG L2 derived feature; an immune system diseases KEGG L2 derived feature; a secretion system KEGG L3 derived feature; a selenocompound metabolism KEGG L3 derived feature; a fructose and mannose metabolism KEGG L3 derived feature; a bacterial chemotaxis KEGG L3 derived feature; an amino acid metabolism KEGG L3 derived feature; a plant-pathogen interaction KEGG L3 derived feature; a bacterial toxins KEGG L3 derived feature; a pyruvate metabolism KEGG L3 derived feature; a general function prediction KEGG L3 derived feature; a nitrogen metabolism KEGG L3 derived feature; a two-component system KEGG L3 derived feature; a ribosome biogenesis KEGG L3 derived feature; a propanoate metabolism KEGG L3 derived feature; a tuberculosis KEGG L3 derived feature; a fatty acid biosynthesis KEGG L3 derived feature; a oxidative phosphorylation KEGG L3 derived feature; a Glyoxylate and dicarboxylate metabolism KEGG L3 derived feature; an Alzheimer's disease KEGG L3 derived feature; a biotin metabolism KEGG L3 derived feature; a pentose phosphate pathway KEGG L3 derived feature; a galactose metabolism KEGG L3 derived feature; a methane metabolism KEGG L3 derived feature; a ribosome biogenesis in eukaryotes KEGG L3 derived feature; a bacterial secretion system KEGG L3 derived feature; a beta-Alanine metabolism KEGG L3 derived feature; a pentose and glucuronate interconversions KEGG L3 derived feature; a polyketide sugar unit biosynthesis KEGG L3 derived feature; a streptomycin biosynthesis KEGG L3 derived feature; a protein export KEGG L3 derived feature; an Aminoacyl-tRNA biosynthesis KEGG L3 derived feature; a chloroalkane and chloroalkene degradation KEGG L3 derived feature; a translation proteins KEGG L3 derived feature; a folate biosynthesis KEGG L3 derived feature; a phosphotransferase system KEGG L3 derived feature; an other transporters KEGG L3 derived feature; a glycerophospholipid metabolism KEGG L3 derived feature; a glycine, serine, and threonine metabolism KEGG L3 derived feature; a terpenoid backbone biosynthesis KEGG L3 derived feature; a riboflavin metabolism KEGG L3 derived feature; a vitamin metabolism KEGG L3 derived feature; a ribosome KEGG L3 derived feature; a homologous recombination KEGG L3 derived feature; a chromosome KEGG L3 derived feature; an inositol phosphate metabolism KEGG L3 derived feature; a naphthalene degradation KEGG L3 derived feature; a phosphatidylinositol signaling system KEGG L3 derived feature; and a taurine and hypotaurine metabolism KEGG L3 derived feature.

19. The method of claim 13, wherein the mental health associated condition comprises an AIDS condition, wherein the microbiome feature dataset comprises a set of microbiome composition features and a set of microbiome functional features,
wherein the set of microbiome composition features is associated with a set of taxa comprising at least one of: Prevotellaceae (family), *Prevotella* (genus), *Megasphaera* (genus), Veillonellaceae (family), Erysipelotrichaceae (family), Erysipelotrichia (class), Erysipelotrichales (order), Bacteroidia (class), Bacteroidetes (phylum), Bacteroidetes/Chlorobi group (superphylum), Bacteroidales (order), Selenomonadales (order), Negativicutes (class), Lachnospiraceae (family), Flavobacteriia (class), Flavobacteriales (order), Flavobacteriaceae (family), *Clostridium* (genus), *Coprococcus* (genus), Porphyromonadaceae (family), *Eubacterium ramulus* (species), Oscillospiraceae (family), Acidaminococcaceae (family), *Lachnospira* (genus), *Barnesiella* (genus), *Phascolarctobacterium* (genus), *Parasutterella* (genus), *Parasutterella excrementihominis* (species), and *Eubacterium ramulus* (species), and wherein the set of microbiome functional features comprises at least one of: a neurodegenerative diseases KEGG L2 derived feature; a transcription KEGG L2 derived feature; a metabolism of cofactors and vitamins KEGG L2 derived feature; an endocrine system KEGG L2 derived feature; a cancers KEGG L2 derived feature; an amino acid metabolism KEGG L2 derived feature; a glycolysis/gluconeogenesis KEGG L3 derived feature; a streptomycin biosynthesis KEGG L3 derived feature; a restriction enzyme KEGG L3 derived feature; a fatty acid biosynthesis KEGG L3 derived feature; a PPAR signaling pathway KEGG L3 derived feature; a phosphotransferase system (PTS) KEGG L3 derived feature; a lipid metabolism KEGG L3 derived feature; an aminobenzoate degradation KEGG L3 derived feature; a pathways in cancer KEGG L3 derived feature; a mismatch repair KEGG L3 derived feature; a vitamin B6 metabolism KEGG L3 derived feature; a butirosin and neomycin biosynthesis KEGG L3 derived feature; a pantothenate and CoA biosynthesis KEGG L3 derived feature; an oxidative phosphorylation KEGG L3 derived feature; a zeatin biosynthesis KEGG L3 derived feature; an energy metabolism KEGG L3 derived feature; a limonene and pinene degradation KEGG L3 derived feature; a valine, leucine, and isoleucine biosynthesis KEGG L3 derived feature; a bacterial chemotaxis KEGG L3 derived feature; a homologous recombination KEGG L3 derived feature; a lipopolysaccharide biosynthesis proteins KEGG L3 derived feature; a transcription machinery KEGG L3 derived feature; and a selenocompound KEGG L3 derived feature.

20. The method of claim 13, wherein the mental health associated condition comprises a colorectal cancer condition, wherein the microbiome feature dataset comprises a set of microbiome composition features and a set of microbiome functional features, wherein the set of microbiome composition features is associated with a set of taxa comprising at least one of: Bacillaceae (family), *Streptococcus* pseudopneumoniae (species), and *Bacteroides fragilis* (species), and wherein the set of microbiome functional features comprises at least one of: a clusters of orthologous groups of proteins (COG) derived feature, a KEGG L2 derived feature, a KEGG L3 derived feature, and a KEGG L4 derived feature.

21. The method of claim 13, wherein providing the therapy comprises providing an interface comprising mental health associated condition information associated with the characterization.

* * * * *